United States Patent [19]

Magerlein

[11] 4,169,197

[45] Sep. 25, 1979

[54] 6-DEOXYNEAMINES AMINOGLYCOSIDE COMPOUNDS

[75] Inventor: Barney J. Magerlein, Portage, Mich.

[73] Assignee: The Upjohn Company, Kalamazoo, Mich.

[21] Appl. No.: 885,872

[22] Filed: Mar. 13, 1978

Related U.S. Application Data

[63] Continuation-in-part of Ser. No. 830,684, Sep. 6, 1977, abandoned.

[51] Int. Cl.$^2$ .......................................... C07H 15/22
[52] U.S. Cl. ...................................... 536/10; 424/180; 536/12; 536/14; 536/17 R; 536/53
[58] Field of Search ................... 536/17, 10, 12, 14

[56] References Cited

U.S. PATENT DOCUMENTS

| | | | |
|---|---|---|---|
| 4,031,210 | 6/1977 | Chazan et al. | 536/17 |
| 4,038,478 | 7/1977 | Magerlein | 536/17 |
| 4,063,015 | 12/1977 | Mallams | 536/17 |
| 4,064,339 | 12/1977 | Coussediere et al. | 536/17 |
| 4,065,616 | 12/1977 | Umezawa et al. | 536/17 |

*Primary Examiner*—Johnnie R. Brown
*Attorney, Agent, or Firm*—Bruce Stein

[57] ABSTRACT

6-Deoxyneamine, 6-deoxy-5-epineamine, their 5-O-glycosyl derivatives, 6-deoxy-5-oxoneamine and the derivatives therefrom are useful as antibacterial agents and/or as intermediates in the synthesis of antibacterially active 6-deoxyneamines.

41 Claims, No Drawings

6-DEOXYNEAMINES AMINOGLYCOSIDE COMPOUNDS

CROSS REFERENCE TO RELATED APPLICATIONS

This patent application is a continuation-in-part of co-pending patent application Ser. No. 830,684, filed Sept. 6, 1977, now abandoned.

BACKGROUND OF THE INVENTION

Aminoglycoside antibacterials containing neamine are well known to those skilled in the art. Two reviews are K. E. Price, et al. *Adv. in Appl. Microbiol.* 17, 191 (1974) and S. Umezawa, *Adv. in Carbohydrates* 30, 111 (1974).

More particularly various deoxyneamines are known. S. Umezawa et al., *J. Antibiotics* 24, 711 (1971) reported the synthesis of 3',4'-dideoxyneamine derivatives. S. Ogawa, et al., *Bull. Chem. Soc. Jap.* 49, 1975 (1976) reported the synthesis and biological activity of 5-deoxyneamines. U.S. Pat. No. 3,963,695 claims 3',4',5,6-tetradeoxyneamines. J. Cleophax et al., *J. Am. Chem. Soc.* 98, 7110 (1976) described the synthesis of 6-deoxyneamine. T. Suami et al., *Carbohydrate Research*, 53, 239 (1977) describe the synthesis of 5- and 6-deoxyneamine and 5,6-dideoxyneamine.

SUMMARY OF THE INVENTION

Refer to Charts A thru D.

Disclosed are compounds of formulas I thru XIX and their pharmaceutically acceptable salts which are useful as antibacterials and/or intermediates to produce the 6-deoxyneamine antibacterials of the present invention.

Also disclosed are various processes useful in the preparation of the 6-deoxyneamines of the present invention. The process for preparing the key intermediate, blocked 6-deoxy-5-oxoneamine (III) is disclosed in Chart A. Chart B discloses various processes of the present invention which prepare the 6-deoxyneamine antibacterials (V, VII, and IX) of the present invention from 6-deoxy-5-oxoneamine (III). Chart C discloses the processes of the present invention which prepare 6-deoxyneamine (XI) and 1-N-alkylated 6-deoxyneamine (XIV) antibacterials from 6-deoxy-5-oxoneamine (III) beginning with reduction of the 5-oxo group. Chart D discloses the process of the present invention which prepare the useful 5-O-glycosyl-6-deoxyneamine antibacterials (XVI and XIX) of the present invention from the 6-deoxyneamine (X) and a glycosyl halide.

Example 40 discloses a process for the preparation of a 3',4'-dideoxy protected starting material (I) from Gentamine $C_{1a}$. An alternative procedure is to begin with the compound 5,6-O-isopropylidene-1,2',3,6'-tetrakis-N-(trifluoroacetyl)-neamine (U.S. Pat. No. 3,996,205, Example 2), convert it to the corresponding 3',4'-sulfonate, eliminate the ester to give a $\Delta^{3'}$-olefin, hydrogenate the $\Delta^{3'}$-olefin and then remove the protective ketal all by means which are well known to those skilled in the art.

DETAILED DESCRIPTION OF THE INVENTION

The 6-deoxyneamine antibacterials (V, VII, IX, XI, XIV, XVI, and XIX) of the present invention are prepared by the processes disclosed in Charts A thru D.

The key intermediate, the 5-oxo compound (III) is prepared by the process of Chart A.

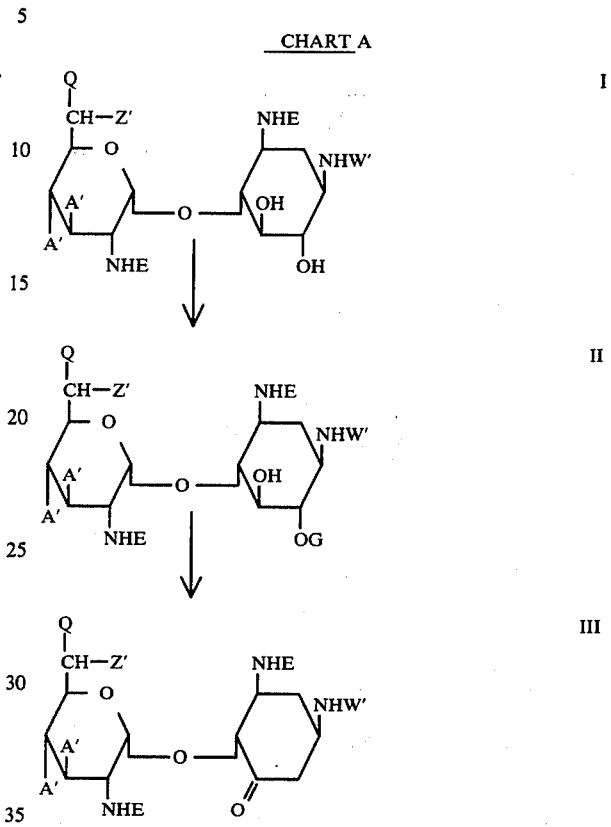

The starting materials for the processes of the present invention are neamine compounds of the formula (I) and are either known to those skilled in the art or readily can be prepared from known compounds by methods well known to those skilled in the art. When Q, Z, E, and A are varied within their definitions the formula (I) compounds include in addition to neamine:

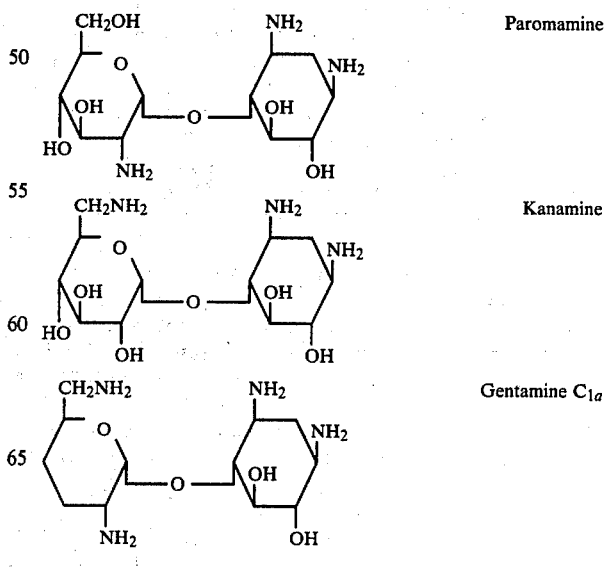

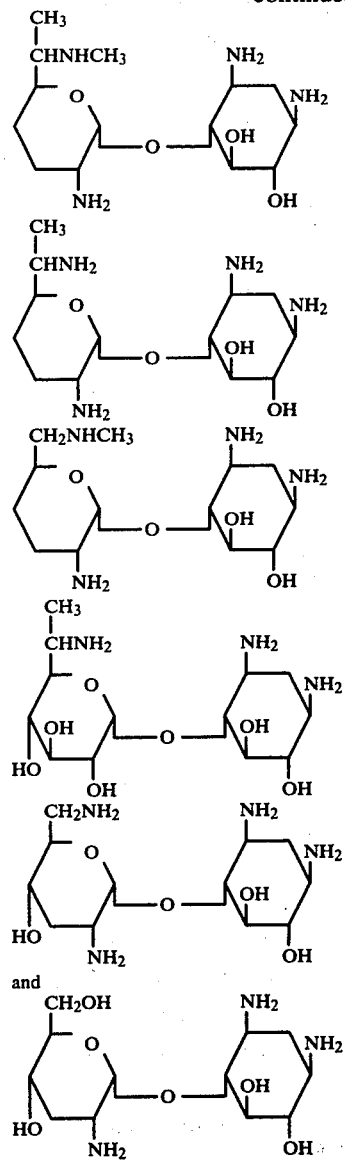

Gentamine C₁

Gentamine C₂

Gentamine C₂ᵦ

Gentamine B₁

Nebramine (Tobramine)

Lividamine

Therefore, when the terms neamine and/or various substituted neamines within the scope of the present invention (I thru XIX) are used, they are deemed equivalent and are meant to include the corresponding paromamine, kanamine, gentamine $C_{1a}$, gentamine $C_1$, gentamine $C_2$, gentamine $C_{2b}$, gentamine $B_1$, nebramine and lividamine type compounds.

It is preferred that Q by hydrogen and Z be amino. It is preferred that A be hydrogen or hydroxyl when unsubstituted (A″) and acetyl or p-nitrobenzoyl when protected (A′). E is a removable amino blocking group. A removable amino blocking group is any group used to block and/or protect an amino group during a subsequent chemical reaction following which it readily can be removed as is well known to those skilled in the art. This includes, for example, trifluoroacetyl, pentafluoropropionyl, acetyl, p-toluenesulfonyl, benzoyl, methanesulfonyl, dichloroacetyl, benzyloxycarbonyl, methoxycarbonyl, ethoxycarbonyl, t-butoxycarbonyl, p-nitrophenyl and 2,4-dinitrophenyl.

In the present invention the removable amino blocking groups are used to protect the 1,2′,3 and 6′ amio groups. The preferred removable amino protecting group is trifluoroacetyl or ethoxycarbonyl. It is most preferred that the amino protecting group is trifluoroacetyl.

When A′ is a hydroxyl group, the compounds of the present invention contain the 3′,4′-dihydroxyl group, which must be protected during the subsquent reactions by a removable alcohol blocking group. A removable alcohol blocking group is any group used to block and/or protect a secondary alcohol group during a subsequent chemical reaction following which it can be readily removed as is well known to those skilled in the art. This includes, for example, (a) saturated or unsaturated, straight or branched chain aliphatic acyl group of 1 thru 18 carbon atoms, including, for example, acetyl, propionyl, butyryl, isobutyryl, t-butyryl, valeryl, caproyl, palmityl, stearyl, oleyl, hexynoyl and the like; (b) saturated or unsaturated alicyclic acyl group of 6 thru 10 carbon atoms, corresponding to the following acids, for example, cyclopentanecarboxylic acid, cyclopentenecarboxylic acid, methylcyclopentenecarboxylic acid, cyclohexanecarboxylic acid and isomers thereof where they exist; (c) saturated or unsaturated alicylic aliphatic acyl group of 7 thru 10 carbon atoms corresponding to the following acids, for example cyclopentaneacetic acid, cyclopentanepropionic acid, cyclohexaneacetic acid, cyclohexanebutyric acid and isomers thereof where they exist; (d) aromatic acyl group of 7–12 carbon atoms corresponding to the following acids, for example, benzoic acid, toluic acid, naphthoic acid, methyl benzoic acid, ethylbenzoic acid and isomers thereof where they exist; (e) aromatic aliphatic acyl group of 8 thru 10 carbon atoms corresponding to the following acids, for example, phenylacetic acid, phenylpropionic acid, cinnamic acid, naphthylacetic acid, and isomers thereof where they exist; (f) the above acyl groups substituted with one or more of the following substituents, which are the same or different, halo (fluorine, chlorine, bromine, iodine), nitro, hydroxy, amino, cyano, thiocyano and alkoxy with an alkyl group of 1 thru 4 carbon atoms. Examples of such substituted carboxylic acids corresponding to the substituted acyl group include, for example:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methylcyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid;

o-, m-, and p-chlorobenzoic acid;
anisic acid;
salicyclic acid;
p-hydroxybenzoic acid;
β-resorcylic acid;
gallic acid;
veratric acid;
trimethoxybenzoic acid;
trimethoxycinnamic acid;
4,4'-dichlorobenzilic acid;
o-, m-, p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid; and
ethoxyformic acid (ethyl hydrogen carbonate).

The preferred removable alcohol blocking group is acetyl and p-nitrobenzoyl.

The neamines (I) are reacted with a sulfonyl chloride of the formula Cl—SO$_2$—R$_7$ to form the 6-sulfonyl ester (II) as is well known to those skilled in the art. It is preferred that the sulfonyl chloride be selected from the group consisting of benzenesulfonyl, p-toluenesulfonyl, methylsulfonyl, trifluoromethylsulfonyl and p-nitrobenzenesulfonyl. The 3'- and 4'-hydroxyl groups as well as the 1,2'- and 3-amino groups must be protected with appropriate alcohol and amino removable blocking groups respectively, prior to the reaction with the sulfonyl chloride. The 6-position must also be properly protected, for example, for lividamine with a removable alcohol blocking group, B, and for neamine with a removable amino blocking group E.

The 6-deoxy-5-oxoneamines (III) are formed by reaction of the 6-sulfonyl ester (II) with a ketone-forming salt. A ketone-forming salt is a salt which when reacted with a 6-sulfonylneamine ester (II) produces a 6-deoxy-5-oxoneamine (III). The wide variety of salts which perform this process is exemplified by the following: sodium iodide, lithium chloride, tetrabutylammonium fluoride and potassium benzoate all of which are operable. It is well in the ability of those skilled in the art to readily determine whether or not a particular salt is a ketone-forming salt without any undue experimentation. Any salt which transforms the 6-sulfonyl ester (II) to the ketone (III) is deemed equivalent to a ketone-forming salt. It is preferred that the ketone-forming salt be sodium iodide. The 6-sulfonyl ester (II) and the ketone-forming salt are heated for several hours (10–30) in an organic diluent such as DMF, hexamethylphosphoramide, dimethylsulfoxide or acetone. The length of heating is somewhat dependent upon the reaction temperature which in turn depends on the boiling point of the organic diluent selected for the reaction as is well known to those skilled in the art.

Chart B shows that the 6-deoxy-5-oxoneamine (III) can be readily converted to an oxime, semicarbazone or hydrazone (IV), alkylated Grignard product (VI), or alkylated Wittig product (VIII) by well-known reactions. When the blocking groups are removed by alkaline hydrolysis from the intermediates (IV, VI, and VIII) the corresponding unblocked oxime, semicarbazone or hydrazone (V), alkylated Grignard product (VII) and alkylated Wittig product (IX) are produced which are useful as antibacterials.

The alcohol and amino blocking groups (B and E respectively) are removed simultaneously by alkaline hydrolysis with any strong aqueous alkali. For example, sodium, potassium, barium, and ammonium hydroxides are suitable. For example, 1 N sodium hydroxide in methanol under reflux for about 15 minutes is particularly advantageous. Following hydrolysis, the organic diluent, such as methanol, may be removed under reduced pressure and the desired unblocked neamine (V, VII, IX, XI, or XVI) is recovered by standard ion exchange procedures. Particularly suitable is CG-50 ion exchange resin (100–200 mesh) in the ammonium form. The column is eluted by gradient elution, the pure product recovered by lyophilization of homogeneous one-spot TLC fractions.

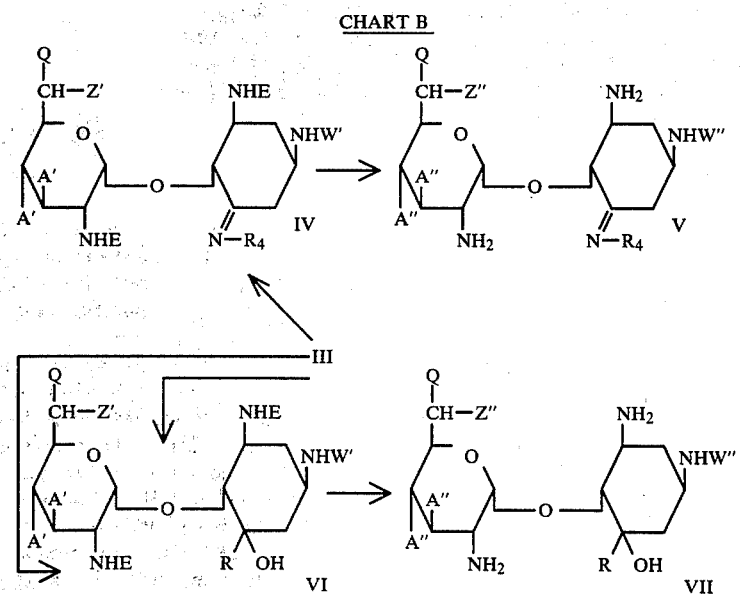

CHART B

CHART B —continued

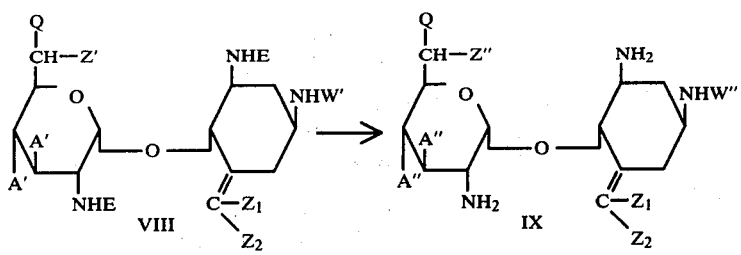

When the 6-deoxy-5-oxoneamine (III) is reacted with a Grignard reagent (R-Mg-X) the alkylated product (VI) is formed. The alkylated product (VI) has a new asymmetric center. By alkaline hydrolysis, as described above, the blocked (Z', A', W') alkylated Grignard intermediate (VI) is transformed into the unblocked (Z", A", W") alkylated Grignard product (VII) which has antibiotic activity.

When the 6-deoxy-5-oxoneamine (III) is reacted with a Wittig reagent, $(C_6H_5)_3P=CZ_1Z_2$, the alkylated intermediate (VIII) is formed. Upon alkaline hydrolysis as described above, the intermediate (VIII) is transformed into the unblocked alkylated Wittig product (IX) which has anti-bacterial activity. In the case where one of the $Z_1$ or $Z_2$ groups has a terminal esterified carboxyl group (carboalkoxy) the alkaline hydrolysis also cleaves the ester portion of the Wittig adduct and depending on work up conditions the isolated product will be the alkylated Wittig product (IX) in its free acid or its anion salt form.

Chart C shows the reduction of the 6-deoxy-6-oxoneamine (III) to the 6-deoxy 5-hydroxy intermediate (X), the hydrolysis of the blocking groups to the unblocked antibacterially active product (XI), the selective blocking of the 6'-amino group when present (XII), formation of the substituted 1-N derivative (XIII) and removal of the 6'-amino blocking group, (M') when present and the terminal amino blocking group (M') of J to give the unblocked 1-N derivative (XIV) which has antibacterial activity.

CHART C

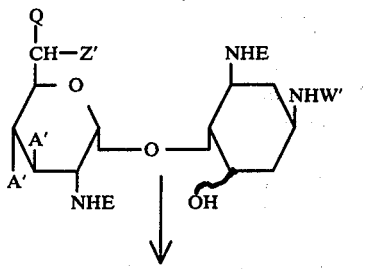

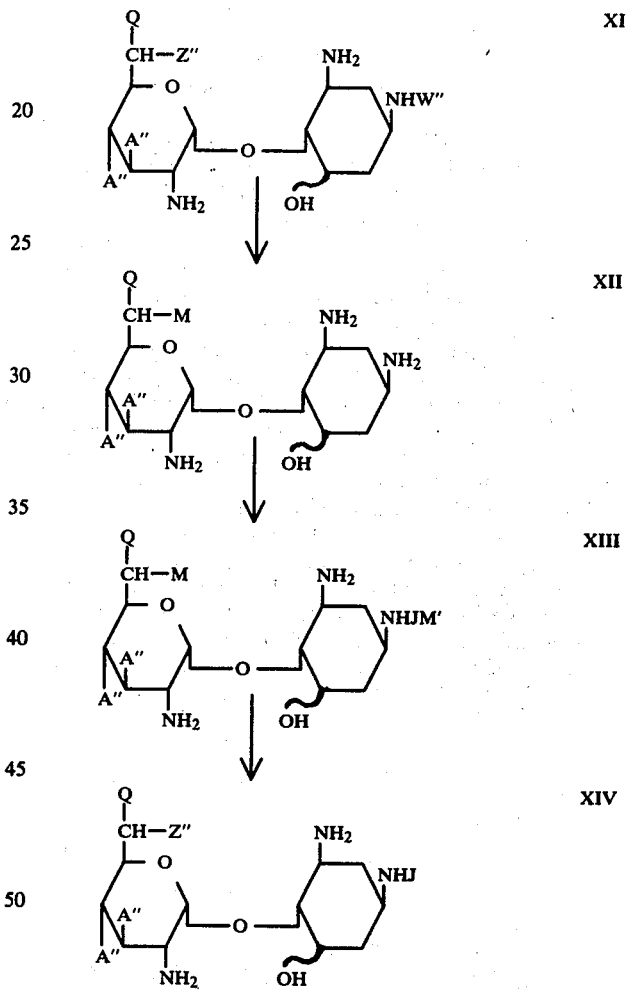

The 6-deoxy-5-oxoneamine (III) is reduced by a number of ketone reducing agents such as sodium cyanoborohydride in THF, sodium borohydride in 2-propanol, aluminum isopropoxide in 2-propanol, diisobutylaluminum hydride, potassium trisec-butylborohydride and hydrogen in the presence of a catalyst. Upon reduction of the 5-oxo group both 5β-hydroxy and 5α-hydroxy epimers are produced. Reduction with sodium cyanoborohydride gives primarily the 5β-hydroxy compound. Catalytic reduction using hydrogen and platinic oxide ($PtO_2$) in methanol produces almost exclusively the 5α-epimer.

Removal of the blocking groups from the intermediate compound of formula (X) by alkaline hydrolysis to give the unblocked antibacterially active compound (XI) is performed as previously described. When it is desired to add a J group to the 1-N position, the 6'-amino groups (—NH$_2$ and —NHCH$_3$) if present must first be protected by a removable selective amino blocking group (M'). If the 6'-position (Z") contains a hydroxyl group (lividamine or paromamine) this group does not have to be blocked during subsequent reactions. The 6'-amino-6-deoxyneamines (XI, Z" is —NH$_2$ or —NHCH$_3$) are reacted with a compound selected from the group disclosed in U.S. Pat. No. 3,781,268, column 5, lines 10-40, by the process described in U.S. Pat. No. 3,781,268, column 5, lines 46-53 and in Examples 6 and 8 thereof, to produce the 6'-protected compound (XII). It is preferred that the 6'-blocking group be N-benzyloxycarbonyloxysuccinimide.

The 6'-protected 6-deoxyneamine (XII) is then 1-N acylated by reaction with a compound of the formula:

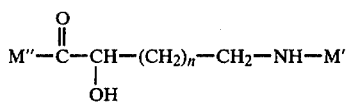

where M" and M' are defined as in U.S. Pat. No. 3,781,268, column 6, lines 22-69 as M and W, respectively, by the process described in U.S. Pat. No. 3,781,268, column 6, line 69 thru column 7, line 2 and in Examples 3 and 9 thereof, to produce the 6'-protected-1-N-acylated 6-deoxyneamine (XIII). The terminal amino blocking group of J and the 6'-blocking group, if present, are then removed by hydrogenolysis using, for example, palladium on charcoal as the catalyst to form the 1-N acylated neamine (XIV). The hydrogenolysis procedure is disclosed in U.S. Pat. No. 3,781,268, column 7, lines 16-35 and in Examples 4 and 10 thereof, and by N. Kawaguchi, et al., *J. Antibiotics*, 25, 695 (1972).

The overall process for the 6'-blocking, 1-N-acylation and subsequent deblocking is outlined very well in U.S. Pat. No. 3,781,268, column 3. The preparation of the removable selective blocking group (M') is described in U.S. Pat. No. 3,781,268 Examples 1 and 5. The preparation of the 1-N acylating agents is described in U.S. Pat. No. 3,781,268 Examples 2, 7 and 11.

The 1-N-aminohydroxybutyric acid (AHBA) derivatives (XIV) of the present invention potentiate the antibacterial activity of the compounds of the present invention and therefore can be used in the same way and for the same purposes as the parent compounds.

The 1-N alkyl derivatives are also useful antibacterials where alkyl includes 1 thru 3 carbon atoms. It is preferred that the 1-N alkyl derivative be ethyl. These secondary amines are formed by methods well known to those skilled in the art for formation of secondary amines.

The 1-N AHBA derivatives (XIV) may also be made by the procedures described by Umezawa, *Adv. Appl. Microbiol.*, 18, 174 (1973).

Alternatively, the 1-N AHBA group can be introduced into the starting neamine (I). See R. Akita et al., *J. Antibiotics* 26, 365 (1973) and Tsukuira, et al., *J. Antibiotics* 26, 365 (1973) and Tsukuira, et al., ibid. at p. 351. If this procedure is utilized, the α-hydroxy group would require blocking at the same time and in the same way as the 3' and 4'-hydroxyl groups. The blocking group at the α-position is removed in the same way as the 3' and 4' blocking groups. Likewise the terminal amino group of 1-N AHBA substituent would also have to be protected or blocked during subsequent reactions that require blocking of the 2',3 and 6'-amino groups. When blocked, the blocking group M' is removed by the process of Examples 4 and 10 of U.S. Pat. No. 3,781,268.

Chart D discloses the preparation of the 6-deoxy-5-O-glycosylneamines (XVI) of present invention as well as the 1-N-AHBA derivatives (XIX) of the 6-deoxy-5-O-glycosylneamines. The 6-deoxy-5-O-glycosylneamines (XV) are prepared by reacting the 6-deoxyneamines (X) with a glycosyl halide of the formula:

CHART D

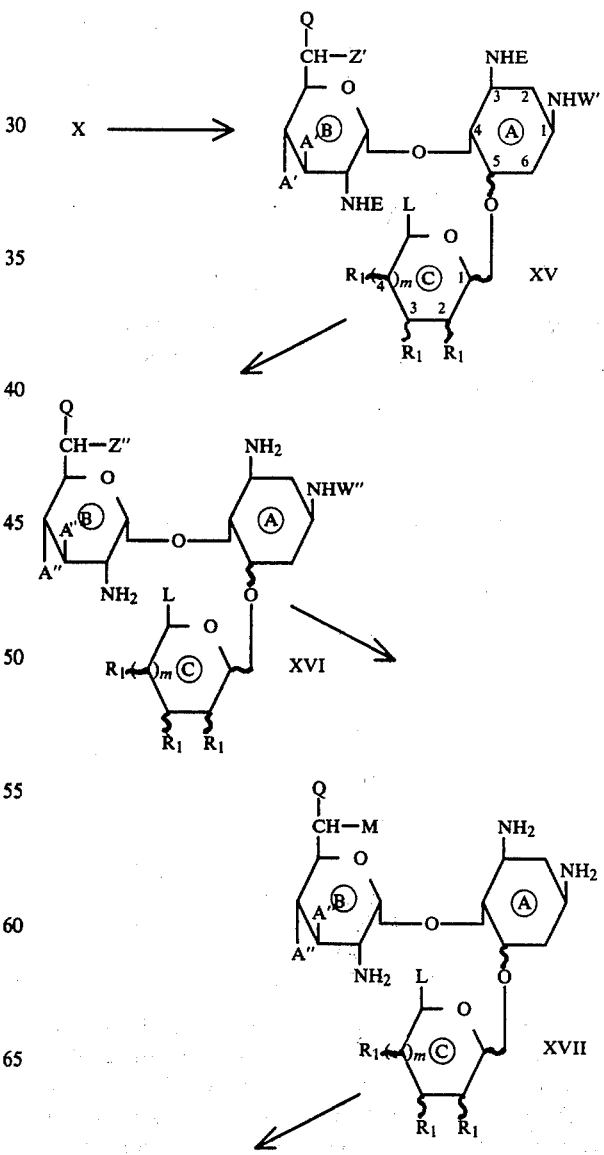

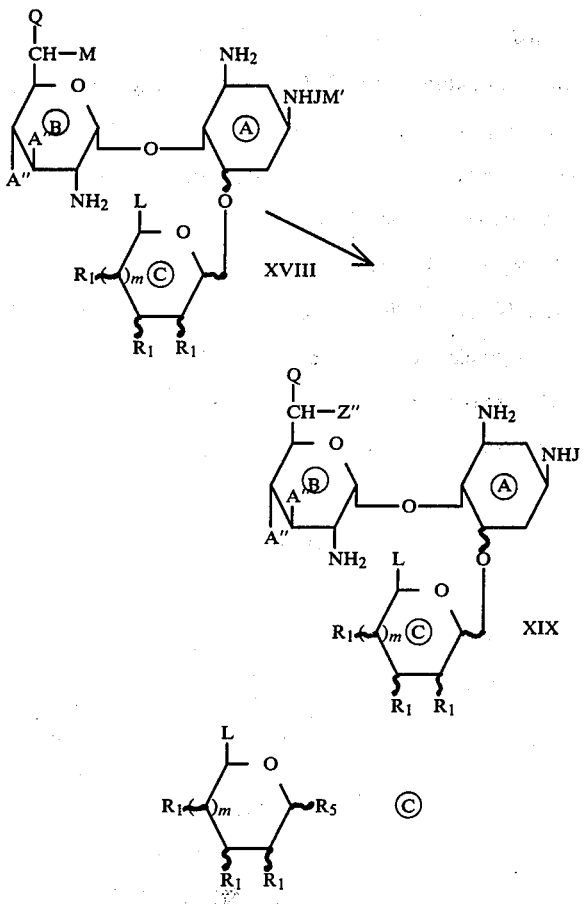

where L, $R_1$, $R_5$, m and ~ are previously defined. The glycosyl halides useful in the present invention are of the formula:

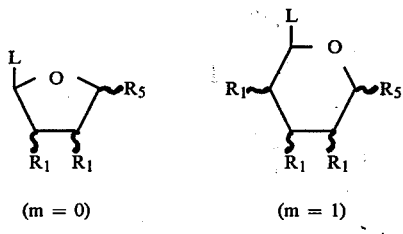

and

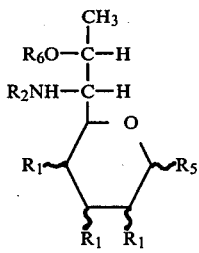

A complete discussion of glycosyl halides is found in *The Amino Sugars*, Vol. 1A, Academic Press, N.Y. (1969) by Jeanloz and by L. J. Haynes and F. H. Newth, "Glycosyl Halides and Their Derivatives", *Advances in Carbohydrate Chemistry*, Vol. 10, Academic Press, 1955, p. 247–254. Examples of glycosyl halides which can be used in the present invention are:

2,3,4,6-tetra-O-acetyl-α-D-altropyranosyl chloride;
2,3,4-tri-O-acetyl-β-L-arabinopyranosyl chloride;
3,4-di-O-acetyl-2-deoxy-D-ribopyranosyl chloride;
2,3,4,6-tetra-O-acetyl-α-D-galactopyranosyl chloride;
2,3,4,6-tetra-O-acetyl-β-D-galactopyranosyl chloride;
2,3,4,6-tetra-O-acetyl-α-D-glucopyranosyl chloride;
2,3,4,6-tetra-O-benzoyl-α-D-glucopyranosyl chloride;
2,3,4,6-tetra-O-acetyl-β-D-glucopyranosyl chloride;
2,3,4,6-tetra-O-acetyl-α-D-mannopyranosyl chloride;
2,3,4,6-tetra-O-benzoyl-α-D-mannopyranosyl chloride;
2,3,4-tri-O-acetyl-α-L-rhamnopyranosyl chloride;
2,3,5-tri-O-acetyl-α-D-ribofuranosyl chloride;
2,3,4-tri-O-benzoyl-α-D-ribopyranosyl chloride;
2,3,4-tri-O-acetyl-β-D-ribopyranosyl chloride;
2,3,4-tri-O-benzoyl-β-D-ribopyranosyl chloride;
2,3,4-tri-O-acetyl-α-D-xylopyranosyl chloride;
2,3,4-tri-O-acetyl-β-D-xylopyranosyl chloride;
2,3,4-tri-O-acetyl-6-deoxy-α-D-glucopyranosyl chloride;
2,3,4-tri-O-acetyl-β-D-arabinopyranosyl bromide;
2,3,4-tri-O-benzoyl-β-D-arabinopyranosyl bromide;
3,4,6-tri-O-acetyl-2-deoxy-α-D-glucopyranosyl bromide;
3,4,6-tri-O-benzoyl-2-deoxy-α-D-glucopyranosyl bromide;
2,3,4-tri-O-acetyl-6-deoxy-α-D-gluocpyranosyl bromide;
1,3,4,5-tetra-O-acetyl-β-D-fructopyranosyl bromide;
1,3,4,5-tetra-O-benzoyl-β-D-fructopyranosyl bromide;
2,3,4,6-tetra-O-acetyl-β-D-galactopyranosyl bromide;
2,3,4,6-tetra-O-acetyl-α-D-glucopyranosyl bromide;
2,3,4-tri-O-acetyl-6-O-benzoyl-α-D-glucopyranosyl bromide;
2,3,4-tri-O-acetyl-6-O-methyl-α-D-glucopyranosyl bromide;
6-O-acetyl-2,3,4-tri-O-benzyl-α-D-glucopyranosyl bromide;
2,3,4,6-tetra-O-acetyl-α-D-mannopyranosyl bromide;
2,3,4,6-tetra-O-benzoyl-α-D-mannopyranosyl bromide;
2,3,4-tri-O-acetyl-α-L-rhamnopyranosyl bromide;
2,3,4-tri-O-benzoyl-α-L-rhamnopyranosyl bromide;
2,3,4-tri-O-acetyl-β-D-ribopyranosyl bromide;
2,3,4-tri-O-benzoyl-β-D-ribopyranosyl bromide;
2,3,4-tri-O-benzoyl-D-xylopyranosyl bromide;
2,3,4-tri-O-acetyl-L-xylopyranosyl bromide;
2,3,4-tri-O-benzoyl-L-xylopyranosyl bromide
2-acetamido-3,4,5-tri-O-acetyl-2-deoxy-α-D-glucopyranosyl bromide;
2-acetamido-3,4,5-tri-O-acetyl-2-deoxy-α-D-glucopyranosyl chloride;
2-acetamido-3,4,5-tri-O-acetyl-2-deoxy-β-D-glucopyranosyl chloride;
2-benzamido-3,4,5-tri-O-benzoyl-2-deoxy-α-D-glucopyranosyl bromide;
3,4,6-tri-O-acetyl-2-benzamido-2-deoxy-α-D-glucopyranosyl chloride;
3,4,6-tri-O-acetyl-2-[(benzyloxycarbonyl)amino]-2-deoxy-α-D-glucopyranosyl bromide;
3,4,6-tri-O-acetyl-2-deoxy-2-(2,4-dinitroanilino)-α-D-glucopyranosyl bromide;
2-acetamido-3,4-di-O-acetyl-2-deoxy-D-ribofuranosyl chloride;
2-acetamido-3,4,6-tri-O-acetyl-2-deoxy-D-galactopyranosyl bromide;
2-acetamido-3,4,6-tri-O-acetyl-2-deoxy-α-D-galactopyranosyl chloride;

3-acetamido-2,4,6-tri-O-acetyl-3-deoxy-α-D-mannopyranosyl bromide;

3-acetamido-2,4,6-tri-O-acetyl-3-deoxy-α-D-mannopyranosyl chloride;

2,4,6-tri-O-acetyl-3-[(benzyloxycarbonyl)amino]-3-deoxy-α-D-glucopyranosyl bromide;

2,3,4-tri-O-acetyl-6-[(benzyloxycarbonyl)amino]-6-deoxy-α-D-glucopyranosyl bromide;

2,4,6-tri-O-acetyl-3-[(benzyloxycarbonyl)amino]-3-deoxy-D-glucopyranosyl chloride;

2,3,4-tri-O-acetyl-6-[(benzyloxycarbonyl)amino]-6-deoxy-D-glucopyranosyl chloride.

The above glycosyl halides are known and available to those skilled in the art, D. Horton, "Monosaccharide Amino Sugars", in *The Amino Sugars*, Vol. 1A, Editor R. W. Jeanloz, Academic Press, N.Y. (1969), p. 204 and in L. J. Haynes and F. H. Newth, *Advances in Carbohydrate Chemistry*, Vol. 10, Academic Press, 1955, pages 147–154. Other glycosyl halides which can be used in the subject invention are N-acetyl-2,3,4,7-tetra-O-acetyl-α and β-lincosaminyl bromides as disclosed by B. Bannister, *J. Chem. Soc.*, Perkin, 3025 (1972). Still other substituted glycosyl halides which can be used in the subject invention are 3-acetamido-2,4,6-tri-O-benzyl-3-deoxyglucopyranosyl chloride [S. Koto et al., *Bull. Chem. Soc. Japan*, 41, 2765 (1968)]; 2,3,4-tri-O-benzyl-6-(N-benzylacetamido)-6-deoxy-α-D-glucopyranosyl chloride [Koto, ibid]; 3-acetamido-2,4,6-tri-O-acetyl-3-deoxyglucopyranosyl bromide [Shibahara, et al., *J. Amer. Chem. Soc.*, 94, 4353 (1972)]; and 3,4,6-tri-O-acetyl-2-trifluoroacetamido-2-desoxy-α-D-glucopyranosyl bromide [Meyer zu Reckendorf et al., *Chem. Ber.*, 103, 1792 (1970)].

The 1-N AHBA and 1-N-alkyl derivatives (XIX) are prepared as described for the formula (XIV) compounds of Chart C, by protecting the 6'-position, if necessary, alkylating the 1-N position and selectively removing the amino blocking groups (M'). Alternatively, as described for the formula (XIV) compounds of Chart C, the 1-N position may be alkylated prior to the reaction of the glycosyl halide forming the 6-deoxy-5-O-glycosylneamine (XV).

The compounds of formulas (I-IV, VI, VIII, X, XII, XIII, XV, XVII and XVIII) are intermediates useful in the preparation of the aminoglycoside antibacterials of the present invention.

The compounds of formulas (V, VII, IX, XI, XIV, XVI, and XIX) are active as antibacterials and can be used in various environments to erradicate or control susceptible microorganisms. Tables I and II set forth the in vitro antibacterial test results for representative compounds of the present invention. The results were obtained with a standard disc plate assay using 12.5 mm paper discs.

TABLE I

| | Zones of Inhibition (mm) | | | | | | | |
|---|---|---|---|---|---|---|---|---|
| | Compound XVβ | | Compound XVα | | Compound XVI | | Neamine | |
| | 1 mg/ml | 0.1 mg/ml | 1 mg/ml | 0.1 mg/ml | 1 mg/ml | 0.1 mg/ml | 1 mg/ml | 0.1 mg/ml |
| *B. cereus* UC® 3145 | 26 | 17 | 20 | — | 18 | — | 24 | 15 |
| *B. subtilis* UC 564 | 39 | 31 | 34 | 25 | 34 | 25 | 39 | 30 |
| *S. aureus* UC 80 | 27 | 19 | 25 | 17 | 21 | T | 29 | 20 |
| *S. lutea* UC 130 | 19 | | 16 | | T | | 17 | |
| *K. pneumoniae* UC 57 | 36 | 28 | 31 | 23 | 24 | T | 34 | 27 |
| *P. vulgaris* UC 93 | 27 | 18 | 23 | T | 18 | | 27 | 18 |
| *E. coli* UC 51 | 27 | 20 | 24 | 17 | 19 | | 27 | 19 |
| *Ps. aeruginosa* UC 95 | 15 | | | | T | | 17 | |
| *S. schottmuelleri* UC 126 | 24 | 16 | 20 | | 15 | | 24 | 16 |
| *S. gallinarum* UC | 29 | 21 | 26 | 17 | 20 | | 29 | 19 |

T = Trace
UC is a registered trademark designating The Upjohn Culture Collection

TABLE II

| | Zones of Inhibition (mm) | | | | | |
|---|---|---|---|---|---|---|
| | 6-Deoxy-5-epineamine (XI) | | 6-Deoxy-5-methyl-neamines (VII) | | Neamine | |
| | 1 mg/ml | 0.1 mg/ml | 1 mg/ml | 0.1 mg/ml | 1 mg/ml | 0.1 mg/ml |
| *B. cereus* UC 3145 | 22 | T | 23 | T | 23 | 15 |
| *B. subtilis* UC 564 | 35 | 26 | 37 | 26 | 37 | 28 |
| *S. aureus* UC 80 | 24 | 17 | 25 | 18 | 26 | 18 |
| *S. gallin.* UC 265 | 27 | 18 | 28 | 18 | 29 | 19 |
| *S. lutea* UC 130 | 17 | — | 15 | — | 17 | — |
| *K. pneumo.* UC 57 | 30 | 23 | 29 | 22 | 32 | 26 |
| *P. vulg.* UC 93 | 24 | T | 24 | T | 28 | 15 |
| *E. coli* UC 51 | 24 | 16 | 24 | 16 | 25 | 18 |
| *Ps. aerug.* UC 95 | 17 | — | 15 | — | 18 | — |
| *S. schott.* UC 126 | 21 | T | 21 | T | 23 | 15 |

The compounds VII, XI, XVβ, XVα and XVI were tested in a standard microplate test in BHI (Brain Heart Infusion) Agar at a concentration of 1 mg./ml. and dilutions thereof at 37° incubation temperature. The end points are read out 20 hours. BHI Agar is supplied by Difco Laboratories, Detroit, Mich. U.S.A. and has the following compositions:

| | |
|---|---|
| Calf brains, infusion from | 200 gm. |
| Beef heart, infusion from | 250 gm. |
| Bacto Proteose-peptone, Difco | 10 gm. |
| Bacto-Dextrose, Difco | 1 gm. |
| Sodium chloride | 5 gm. |
| Disodium phosphate | 2.5 gm. |
| Agar | 15 gm. |

The results are given in Tables III and IV.

TABLE III

| | Minimum Inhibitory Concentration (mcg/ml) | | |
|---|---|---|---|
| | 6-deoxy-5-methylneamine (VII) | 6-deoxyneamine (XI) | Neamine |
| S. aureus UC 76 | 15.6 | 3.9 | 3.9 |
| S. pyogenes UC 152 | 7.8 | 15.6 | 7.8 |
| S. faecalis UC 694 | >500 | >500 | >500 |
| S. pneumoniae I UC 41 | 62.5 | 62.5 | 62.5 |
| E. coli UC 45 | 125 | 31.2 | 62.5 |
| K. pneumoniae UC 58 | 15.6 | 7.8 | 15.6 |
| S. schottmuelleri UC 126 | 62.5 | 31.2 | 31.2 |
| Ps. aeruginosa UC 95 | >500 | >500 | >500 |
| P. vulgaris UC 93 | 62.5 | 31.2 | 62.5 |
| P. mirabilis UC 6671 | 250 | 62.5 | 62.5 |
| P. morganii UC 3186 | 125 | 62.5 | 62.5 |
| P. rettgeri UC 339 | >500 | 250 | 250 |
| S. marcescens UC 131 | 125 | 250 | 250 |
| S. flexneri UC 143 | 125 | 62.5 | 62.5 |
| S. typhi UC 215 | 62.5 | 31.2 | 15.6 |

TABLE IV

| | Minimal Inhibitory Concentration (μg/ml) | | | |
|---|---|---|---|---|
| | * (XVI) | ** (XVβ) | *** (XVα) | Neamine |
| S. aureus UC 76 | 250 | 31.2 | 125 | 7.8 |
| S. pyogenes UC 152 | 250 | 3.9 | 31.2 | 7.8 |
| S. fecalis UC 694 | >500 | 500 | >500 | >500 |
| D. pneumoniae UC 41 | >500 | 15.6 | 125 | 62.5 |
| E. coli UC 311 | >500 | 31.2 | 250 | 125 |
| K. pneumoniae UC 58 | 125 | 2.0 | 15.6 | 7.8 |
| S. schottmuelleri UC 126 | >500 | 7.8 | 125 | 15.6 |
| Ps. aeruginosa UC 95 | >500 | >500 | >500 | >500 |
| P. vulgaris UC 93 | >500 | 31.2 | 500 | 62.5 |
| P. mirabilis UC 6671 | >500 | 125 | >500 | 250 |
| P. morganii UC 3186 | 250 | 7.8 | 125 | 31.2 |
| P. rettgeri UC 339 | >500 | >500 | >500 | >500 |
| S. marcescens UC 131 | >500 | 62.5 | 500 | 250 |
| S. flexneri UC 143 | >500 | 31.2 | 500 | 125 |
| S. typhi UC 215 | >500 | 15.6 | 62.5 | 31.2 |

*0-2,6-Diamino-2,6-dideoxy-α-D-glucopyranosyl(1→4)-0-[3-amino-2,3-dideoxy-α-D-arabinohexopyranosyl(1→5)]-2,6-dideoxy-D-streptamine.
**0-2,6-Diamino-2,6-dideoxy-α-D-glycopyranosyl(1→4)-0-[β-D-ribofuranosyl(1→5)]-2,6-dideoxy-D-streptamine.
***0-2,6-Diamino-2,6-dideoxy-α-D-glycopyranosyl(1→4)-0-[α-D-ribofuranosyl(1→5)]-2,6-dideoxy-D-streptamine.

Therefore, the antibacterially active compounds in the present invention are useful to treat woolen felts in the paper industries since B. cereus has been isolated from deteriorated woolen felts. Further the compounds of the present invention are useful for controlling the infection of silk worms (B. subtilis) and useful to minimize or prevent odor in fish and in fish crates both caused by B. subtilis. The compounds of the present invention shown to be active against E. coil can be used to reduce, arrest, and erradicate slime production in paper mill systems and also to prolong the life of cultures of Trichomonas foetus, T. hominis and T. vaginalis by freeing then of E. coli contamination. Further since some of the compounds of the present invention are active against S. hemolyticus they can be used to disinfect instruments, utensils, or surfaces where the inactivation of this microorganism is desirable.

The pharmaceutically acceptable salts of the 6-deoxyneamine antibacterials of the present invention are made by reacting the parent (free base) 6-deoxyneamine with a stoichiometric amount of a pharmaceutically acceptable acid. Examples of such acids are hydrochloric, sulfuric, phosphoric, nitric, hydrobromic, acetic, ascorbic, malic, citric, and palmitic.

The definitions and explanations below are for the terms as used throughout the entire patent application including both the specification and claims.

All temperatures are in degrees Centigrade.
TLC refers to thin-layer chromatography.
THF refers to tetrahydrofuran.
DMF refers to dimethylformamide.
SSB refers to a mixture of isomeric hexanes.
Amberlite ® (a trademark of the Rohm & Haas Co., Philadelphia, Pa., U.S.A.) CG-50 refers to a chromatographic grade of a weakly acidic carboxylic (polymethacrylic) type cation exchange resin (100–200 mesh) marketed by Mallinckrodt Chemical Works, St. Louis, Mo., U.S.A.
IR refers to infrared spectroscopy.
UV refers to ultraviolet spectroscopy.
CMR refers to carbon-13 magnetic resonance spectroscopy, chemical shifts are reported in ppm (δ) downfield from TMS.
NMR refers to nuclear (proton) magnetic resonance spectroscopy, chemical shifts are reported in ppm (δ) downfield from TMS.
TMS refers to tetramethylsilane.
$[\alpha]_D^{25}$ refers to the angle of rotation of plane polarized light (specific optical rotation) at 25° with the sodium D line (5893A).
Pharmaceutically acceptable refers to those properties and/or substances which are acceptable to the patient from a pharmacological-toxicological point of view and to the manufacturing pharmaceutical chemist from a physical-chemical point of view regarding composition, formulation, stability, patient acceptance and bioavailability.
When solvent pairs are used, the ratio of solvents used are volume/volume (v/v).
A' is a hydrogen atom or —OB group.
A" is a hydrogen atom or hydroxyl group.
B is a removable alcohol blocking group.
E is a removable amino blocking group.
G is —SO$_2$—R$_7$.
J is an alkyl group of 1 thru 3 carbon atoms or

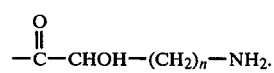

L is —CH$_2$R$_1$ or

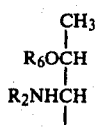

with the proviso that when L is

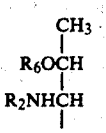

m is 1 and $R_1$ is —O-acetyl.

M is —NHM', —NCH$_3$M' or hydroxyl.

M' is a removable selective amino blocking group the scope of which is incorporated by reference to U.S. Pat. No. 3,781,268, column 6, lines 1–22.

Q is a hydrogen atom or methyl.

R is alkyl 1 thru 4 carbon atoms or phenyl.

$R_1$ is selected from the group consisting of a hydrogen atom, hydroxyl, —O-acetyl, —O-benzyl, —O-benzoyl, —NHR$_2$, —NR$_2$R$_3$.

$R_2$ is a hydrogen atom, acetyl or trifluoroacetyl.

$R_3$ is alkyl of 1 thru 4 carbon atoms.

$R_4$ is hydroxy, amino or —NHCONH$_2$.

$R_5$ is a chlorine or bromine atom.

$R_6$ is a hydrogen atom or acetyl.

$R_7$ is alkyl of 1 thru 3 carbon atoms substituted with 0–3 substituents which are the same or different and are selected from the group consisting of a fluorine or chlorine atom; phenyl substituted with 0–2 substituents which are the same or different and are selected from the group consisting of a chlorine atom and a methyl, nitro or methoxy group.

W' is E or J.

W" is J or a hydrogen atom.

X is a chlorine, bromine, or iodine atom.

Z' is —NHE, —OB or —NCH$_3$E.

Z" is amino, hydroxyl or methylamino.

$Z_1$ and $Z_2$ are the same or different and are hydrogen, alkyl of 1 thru 4 carbon atoms, $Z_1$ and $Z_2$ can be joined together with the attached carbon atoms to form a cycloalkyl ring of 5–6 carbon atoms; if one of $Z_1$ or $Z_2$ are hydrogen and the other alkyl, the alkyl group may terminate with carboalkoxy or alkoxy.

m is zero or 1.

n is an integer of 0 thru 2.

~ indicates the attached substituent is in either the α or β configuration.

Ketone-forming salt is a salt which when reacted with a 6-sulfonylneamine ester (II) produces a 6-deoxy-5-oxo-neamine (III).

Saline refers to an aqueous saturated sodium chloride solution.

HPLC refers to high pressure liquid chromatography.

EXAMPLES

The invention may be more fully understood from the following examples which are illustrative of the process and compounds of the present invention but are not to be construed as limiting.

EXAMPLE 1

3',4'-Di-O-acetyl-1,2',3,6'-tetrakis-N-(trifluoroacetyl)-neamine [Formula I: Q is a hydrogen atom; Z' is a —NHE group; E is trifluoroacetyl; A' is an —OB group; B is acetyl and W' is E]

A.
3',4'-Di-O-acetyl-5,6-O-isopropylidene-1,2',3,6'-tetrakis-N-(trifluoroacetyl)-neamine 5,6-O-Isopropylidene-1,2',3,6'-tetrakis-N-(trifluoroacetyl)-neamine (U.S. Pat. No. 3,984,393, Example 2, 5.0 g.) in acetic anhydride (15 ml.) and pyridine (15 ml.) are stirred at about 22° for 17 hours. After work-up there is obtained 3',4'-di-O-acetyl-5,6-O-isopropylidene-1,2',3,6'-tetrakis-N-(trifluoroacetyl)-neamine. IR (neat) 3400, 1760, 1725, 1560 and 1160–1240 cm$^{-1}$; NMR (acetone-d$_6$) 1.34, 1.91, 1.97, 3.1–4.5 and 5.42 δ.

B.
3',4'-Di-O-acetyl-1,2',3,6'-tetrakis-N-(trifluoroacetyl)-neamine

3',4'-Di-O-acetyl-5,6-O-isopropylidene-1,2',3,6'-tetrakis-N-(trifluoroacetyl)-neamine (8.3 g.), acetic acid (56 ml.) and water (30 ml.) are heated at 80° for 1 hour and cooled. The diluent is evaporated under reduced pressure. The residue is dissolved in ethyl acetate-methylene chloride. After washing with water and bicarbonate solution the filtrate is concentrated under reduced pressure. The residue is column chromatographed on silica gel (500 g.) using chloroform-methanol (10:1) for elution. Homogeneous one-spot TLC fractions corresponding to the desired product are pooled and concentrated to give the title compound IR (neat) 3250–3700, 1720, 1760, 1560, 1220, 1580 and 1560 cm$^{-1}$; NMR (acetone-d$_6$) 1.90, 1.98, 3.4–4.5, and 5.5 δ.

EXAMPLE 2

3',4'-Di-O-acetyl-6-O-p-toluenesulfonyl-1,2',3,6'-tetrakis-N-(trifluoroacetyl)-neamine [Formula II: Q is a hydrogen atom; Z' is a —NHE group; E is trifluoroacetyl; A' is an —OB group; B is acetyl; W' is E and G is p-toluenesulfonyl]

Refer to Chart A.

3'4'-Di-O-acetyl-1,2',3,6'-tetrakis-N-(trifluoroacetyl)-neamine (I, Example 1, 20 g.) is dissolved in anhydrous pyridine (240 ml.). p-Toluenesulfonic acid (24.2 g.) is added with stirring to the above solution. After stirring for 20 hours at room temperature (20°–25°) a small amount of ice is added and the mixture cooled to keep the temperature less than 30°. When no further heat effect is noted, methylene chloride (500 ml.) and ethyl acetate (250 ml.) are added followed by hydrochloric acid (6 N, 480 ml.). The organic layer is separated, washed twice with dilute hydrochloric acid, then water and finally with potassium bicarbonate solution. The organic layer is dried and concentrated under reduced pressure to yield 23.2 g. This material is chromatographed on silica gel (2 kg.) with chloroform-methanol (10:1). Homogeneous one-spot TLC fractions are pooled and concentrated to give the title compound. CMR (acetone-d$_6$) 20.38, 21.41, 32.03, 40.36, 49.01, 50.26, 53.73, 69.49, 69.83, 71.45, 74.19, 82.71, 83.86, 99.47, 109.70, 124.06, 128.71, 130.44, 134.80, 145.89, 154–162, 170.29 and 170.75 δ.

EXAMPLE 3

3',4'-Di-O-p-nitrobenzoyl-6-O-p-toluenesulfonyl-1,2',3,6'-tetrakis-N-(trifluoroacetyl)-neamine [Formula II: Q is a hydrogen atom; Z' is a —NHE group; E is a trifluoroacetyl; A' is an —OB group; B is p-nitrobenzoyl; W' is E and G is p-toluenesulfonyl]

Refer go Chart A.

3',4'-Di-O-p-nitrobenzyl-1,2',3,6'-tetrakis-N-(trifluoroacetyl)-neamine (I, U.S. Pat. No. 3,984,393, Example 4, 10.0 g.) and p-toluenesulfonyl chloride (9.8 g.) in pyridine (40 ml.) is mixed overnight at about 25°. The reaction mixture is diluted with water and then extracted with a methylene chloride-ethyl acetate mixture. The mixture is concentrated under reduced pressure to yield a crude product. The crude product is column chromatographed over silica gel (200 g.) using chloroform-methanol (15:1). Homogeneous one-spot TLC fractions are pooled and concentrated to give the title compound. CMR (acetone-$d_6$) 21.50, 32.23, 40.43, 49.14, 50.38, 53.80, 69.60, 71.10, 73.64, 74.45, 82.91, 83.86, 99.64, 109, 124.43–151.80, 153–160, 164.56 and 165.08 δ; $[\alpha]_D$ −43° (ethanol).

EXAMPLE 4

3',4'-Di-O-acetyl-5,6-dideoxy-5-oxo-1,2',3,6'-tetrakis-N-(trifluoroacetyl)-neamine [Formula III: Q is a hydrogen atom; Z' is a —NHE group; E is trifluoroacetyl; A' is a —OB group; B is acetyl and W' is E]

Refer to Chart A.

3',4'-Di-O-acetyl-6-O-p-toluenesulfonyl-1,2',3,6'-tetrakis-N-(trifluoroacetyl)-neamine (II, Example 2, 9.84 g.) and sodium iodide (13.7 g.) are heated in DMF at 95° for 17 hours. After heating, the DMF is removed by reduced pressure and the residue is partitioned in a mixture of ethyl acetate-benzene-water (4:4:1). The organic layer is washed 4 times with water, twice with sodium thiosulfate, once again with water, dried over sodium sulfate and then concentrated under reduced pressure to yield the crude product. The crude product is column chromatographed over silica gel (1.1 kg.) eluting with SSB-ethyl acetate (1:1). Homogeneous one-spot TLC fractions containing the title compound are pooled and concentrated under reduced pressure to give the title compound. CMR (acetone-$d_6$) 20.49, 35.71, 39.98, 45.69, 45.75, 51.08, 53.24, 69.15, 69.36, 71.31, 82.60, 97.97, 95.47, 109.78, 124.14, 138.5, 156–163, 170.75 and 209 δ; $[\alpha]_D$ +70° (acetone).

EXAMPLE 5

3',4'-Di-O-p-nitrobenzoyl-5,6-dideoxy-5-oxo-1,2',3,6'-tetrakis-N-(trifluoroacetyl)-neamine [Formula III: Q is a hydrogen atom; Z' is a —NHE group; E is trifluoroacetyl; A' is an —OB group; B is p-nitrobenzoyl and W' is E]

Refer to Chart A.

Following the general procedure of Example 4 and making non-critical variations but substituting 3',4'-di-O-p-nitrobenzoyl-6-O-p-toluenesulfonyl-1,2',3,6'-tetrakis-N-(trifluoroacetyl)-neamine (II, Example 3) for 3',4'-di-O-acetyl-6-O-p-toluenesulfonyl-1,2',3,6'-tetrakis-N-(trifluoroacetyl)-neamine there is obtained the title compound. CMR (acetone-$d_6$) 35.82, 40.07, 45.69, 45.77, 51.03, 53.12, 69.25, 71.04, 73.37, 82.73, 97.93, 124.44, 131.69, 135.46, 151.84, 155–162, 164.28, 165.06 and 209 δ; $[\alpha]_D$ −54° (methanol); UV (methanol) λmax. =257 nm (ε=26,750) and 304 nm (ε=2,950).

EXAMPLE 6

3',4'-Di-O-acetyl-5,6-dideoxy-5-oximido-1,2',3,6'-tetrakis-N-(trifluoroacetyl)-neamine [Formula IV: Q is a hydrogen atom; Z' is a —NHE group; E is trifluoroacetyl; A' is an —OB group; B is acetyl; W' is E and $R_4$ is hydroxyl]

Refer to Chart B.

3',4'-Di-O-acetyl-5,6-dideoxy-5-oxo-1,2',3,6'-tetrakis-N-(trifluoroacetyl)-neamine (III, Example 4), methanol, sodium bicarbonate, water and hydroxylamine hydrochloride are refluxed until TLC shows the reaction is complete. After usual work up procedures the title compound is obtained.

EXAMPLE 7

3',4'-Di-O-acetyl-5,6-dideoxy-5-hydrazono-1,2',3,6'-tetrakis-N-(trifluoroacetyl)-neamine [Formula IV: Q is a hydrogen atom; Z' is a —NHE group; E is trifluoroacetyl; A' is an —OB group; B is acetyl; W' is E and $R_4$ is amino]

Refer to Chart B.

3',4'-Di-O-acetyl-5,6-dideoxy-5-oxo-1,2',3,6'-tetrakis-N-(trifluoroacetyl)-neamine (III, Example 4) is reacted with hydrazine until TLC shows the reaction is complete. After usual work up procedures the title compound is obtained.

EXAMPLE 8

3',4'-Di-O-acetyl-5,6-dideoxy-5-semicarbazono-1,2',3,6'-tetrakis-N-(trifluoroacetyl)-neamine [Formula IV: Q is a hydrogen atom; Z' is a —NHE group; E is trifluoroacetyl; A' is an —OB group; B is acetyl; W' is E and $R_4$ is —NHCONH$_2$]

Refer to Chart B.

3'4'-Di-O-acetyl-5,6-dideoxy-5-oxo-1,2',3,6'-tetrakis-N-(trifluoroacetyl)-neamine (III, Example 4), methanol, sodium aetate, water and semicarbazide hydrochloride are refluxed until TLC shows the reaction is complete. After usual work up procedures the title compound is obtained.

EXAMPLE 9

5,6-Dideoxy-5-oximido-neamine [Formula V: Z" is amino; A" is hydroxyl; Q, and W'" are hydrogen atoms and $R_4$ is hydroxyl]

Refer to Chart B.

Following the general procedure of Example 13, and making non-critical variations but substituting 3',4'-di-O-acetyl-5,6-dideoxy-5-oximido-1,2',5,6'-tetrakis-N-(trifluoroacetyl)-neamine (IV, Example 6) for 3,4'-di-O-acetyl-6-deoxy-5-methyl-1,2',3,6'-tetrakis-N-(trifluoroacetyl)-neamine the title compound is obtained.

EXAMPLE 10

5,6-Dideoxy-5-hydrazono-neamine [Formula V: Z" is amino; A" is hydroxyl; Q, and W'" are hydrogen atoms and $R_4$ is amino]

Refer to Chart B.

Following the general procedure of Example 13, and making non-critical variations but substituting 3',4'-di-O-acetyl-5,6-dideoxy-5-hydrazono-1,2',3,6'-tetrakis-N-(trifluoroacetyl)-neamine (IV, Example 7) for 3',4'-di-O-acetyl-6-deoxy-5-methyl-1,2',3,6'-tetrakis-N-(trifluoroacetyl)-neamine the title compound is obtained.

EXAMPLE 11

5,6-Dideoxy-5-semicarbazono-neamine [Formula V: Z" is amino; A" is hydroxyl; Q, and W'" are hydrogen atoms, and $R_4$ is —NHCONH$_2$]

Refer to Chart B.

Following the general procedure of Example 13, and making non-critical variations but substituting 3',4'-di-O-acetyl-5,6-dideoxy-5-semicarbazono-1,2',3,6'-tetrakis-N-(trifluoroacetyl)-neamine (IV, Example 8) for 3',4'-di-O-acetyl-6-deoxy-5-methyl-1,2',3,6'-tetrakis-N-(trifluoroacetyl)-neamine the title compound is obtained.

EXAMPLE 12

3',4'-Di-O-acetyl-6-deoxy-5-methyl-1,2',3,6'-tetrakis-N-(trifluoroacetyl)-neamine [Formula VI: Q is hydrogen atom; Z' is a —NHE group; W' is E; E is trifluoroacetyl; A' is an —OB group; B is acetyl; and R is methyl]

Refer to Chart B.

A solution of 3',4'-di-O-acetyl-5,6-dideoxy-5-oxo-1,2',3,6'-tetrakis-N-(trifluoroacetyl)-neamine (III, Example 4) in THF (40 ml.) at 0° is reacted with a slight excess of methyl magnesium bromide as indicated by the appearance of a pink color due to a few drops of 4-phenylazodiphenylamine indicator. Dilute hydrochloric acid is added and the THF removed at reduced pressure. The residue is extracted with ethyl acetate which is column chromatographed over silica gel eluting with ethyl acetate-SSB. Homogeneous one-spot TLC fractions are pooled and concentrated to give the title compound. CMR (acetone-$d_6$) 20.57, 28.45, 37.12, 40.12, 43.56, 44.61, 50.35, 54.13, 69.61, 70.04, 70.63, 72.86, 84.83, 98.00, 96, 109.86, 124.22, 138, 154–162, 170.52 and 171.41 $\delta$ $[\alpha]_D$ +64 (acetone).

EXAMPLE 13

6-Deoxy-5-methyl-neamine [Formula VII: Z" is amino; A" is hydroxyl; Q and W" are hydrogen atoms; R is methyl]

Refer to Chart B.

3',4'-Di-O-acetyl-6-deoxy-5-methyl-1,2',3,6'-tetrakis-N-(trifluoroacetyl)-neamine (VI, Example 12, 1.35 g.) and sodium hydroxide (800 mg.) in aqueous methanol (20 ml., 50%) are refluxed for 15 minutes and cooled. Water (45 ml.) and hydrochloric acid (1 N, 10 ml.) are added to the solution. The resulting mixture is passed over an Amberlite ® CG-50 ion exchange resin (100-200 mesh) in the ammonium form.

The column is eluted with a gradient of water (130 ml.) and ammonium hydroxide (0.5 N, 130 ml.) followed by a gradient of 0.5 N ammonium hydroxide (130 ml.) and 2 N ammonium hydroxide (130 ml.). The fractions are monitored by TLC (chloroform-methanol-ammonium hydroxide, 3:4:2). Homogeneous one-spot TLC fractions are pooled and lyophilized to give the title compound. CMR ($D_2O$) 28.83, 42.22, 42.83, 44.63, 47.52, 50.35, 57.34, 72.46, 74.50, 74.65, 90.87, and 102.09$\delta$.

EXAMPLE 14

3',4'-Di-O-p-nitrobenzoyl-5,6-dideoxy-5-carboethoxymethylidene-1,2',3,6'-tetrakis-N-(trifluoroacetyl)-neamine [Formula VIII: Q and $Z_1$ are hydrogen atoms; Z' is a —NHE group; E is trifluoromethyl; A' is an —OB group; B is p-nitrobenzoyl; W' is E, and $Z_2$ is —COOC$_2$H$_5$]

Refer to Chart B.

3',4'-Di-O-p-nitrobenzoyl-5,6-dideoxy-5-oxo-1,2',3,6'-tetrakis-N-(trifluoroacetyl)-neamine (III, Example 5, 97 mg.) and carboethoxymethylene triphenylphosphorane (70 mg.) in acetonitrile (10 ml.) are refluxed for 30 minutes. TLC (chloroform-methanol, 10:1) shows no starting ketone (III) and a product which is slightly less polar and which reacts with Lemieux Reagent. The title compound is isolated by normal work up methods.

EXAMPLE 15

5,6-Dideoxy-5-carboxymethylideneneamine [Formula IX: Z" is amino; A" is hydroxyl; Q, W"', and $Z_1$ are hydrogen atoms; $Z_2$ is —COOH]

Refer to Chart B.

Following the general procedure of Example 13 and making non-critical variations but substituting 3',4'-di-O-p-nitrobenzoyl-5,6-dideoxy-5-carboethoxymethylidene-1,2',3,6'-tetrakis-N-(trifluoroacetyl)-neamine (VIII, Example 14) for 3',4'-di-O-acetyl-6-deoxy-5-methyl-1,2',3,6'-tetrakis-N-(trifluoroacetyl)-neamine there is obtained the title compound.

EXAMPLE 16

3',4'-Di-O-acetyl-6-deoxy-1,2',3,6'-tetrakis-N-(trifluoroacetyl)-neamine [Formula X: Q is a hydrogen atom; Z' is a —NHE group; E is trifluoroacetyl; A' is an —OB group; B is acetyl; W' is E and ~ is in the $\beta$ configuration]

Refer to Chart C.

3',4'-Di-O-acetyl-5,6-dideoxy-5-oxo-1,2',3,6'-tetrakis-N-(trifluoroacetyl)-neamine (III, Example 4, 600 mg.) and sodium cyanoborohydride (350 ml.) are stirred in THF (23 ml.) along with a few crystals of methyl orange. Hydrogen chloride in THF is added dropwise with stirring to the mixture until a pink color is maintained for 20 minutes. The THF is removed under reduced pressure and the residue is dissolved in ethyl acetate-methylene chloride which is washed well with water. The organic diluents are removed under reduced pressure and the product is column chromatographed over silica gel (100 g.) using chloroform-methanol (20:1). Homogeneous fractions corresponding to the title compound as measured by TLC, chloroform-methanol (10:1), are pooled and concentrated under reduced pressure to yield the title compound. CMR (acetone-$d_6$) 20.44, 20.58, 36.14, 39.08, 40.63, 45.26, 51.20, 54.15, 69.70, 69.83, 70.42, 85.71, 99.66, 96, 110, 124.06, 139, 154–162, 170.43, and 170.73$\delta$.

EXAMPLE 17

3',4'-Di-O-p-nitrobenzoyl-6-deoxy-1,2',3,6'-tetrakis-N-(trifluoroacetyl)-neamine [Formula X: Q is a hydrogen atom; Z' is a —NHE group; E is trifluoroacetyl; A' is an —OB group; B is p-nitrobenzoyl; W' is E and $\delta$ is $\beta$]

Refer to Chart C.

Following the general procedure of Example 16 and making non-critical variations but substituting 3',4'-di-O-p-nitrobenzoyl-5,6-dideoxy-5-oxo-1,2',3,6'-tetrakis-N-(trifluoroacetyl)-neamine (III, Example 5) for 3',4'-di-O-acetyl-5,6-dideoxy-5-oxo-1,2',3,6'-tetrakis-N-(trifluoroacetyl)-neamine there is obtained the title compound. CMR (acetone-$d_6$) 36.30, 39.33, 40.50, 45.32, 51.29, 54.11, 69.86, 71.14, 71.68, 73.77, 85.83, 99.84, 124.46, 131.67, 135.33, 135.55, 151.85, 154–162, 164.59 and 165.13$\delta$.

EXAMPLE 18

3',4'-Di-O-acetyl-6-deoxy-5-epi-1,2',3,6'-tetrakis-N-(trifluoroacetyl)-neamine [Formula X: Q is a hydrogen atom; Z' is a —NHE group; E is trifluoroacetyl; A' is an —OB group; B is acetyl; W' is E and ~ is in the $\alpha$ configuration]

Refer to Chart C.

3',4'-Di-O-acetyl-5,6-dideoxy-5-oxo-1,2',3,6'-tetrakis-N-(trifluoroacetyl)-neamine (III, Example 4, 1.0 g.) and platinic oxide (PtO$_2$, 0.5 g.) in methanol (40 ml.) is shaken under 40 psi of hydrogen for 3 hours. Platinic oxide (0.5 g.) is added and the mixture shaken again under 40 psi of hydrogen for 2.5 hours. The catalyst is removed by filtration and the filtrate concentrated under reduced pressure. The residue is column chromatographed over silica gel (100 g.) eluting with chloroform-methanol (10:1). Homogeneous one-spot fractions are pooled and concentrated under vacuum to give the title compound. CMR (acetone-$d_6$) 20.47, 36.26, 36.56, 40.41, 44.09, 48.14, 53.11, 65.32, 68.60, 69.88, 71.53, 138.6, 155–162 and 170.59$\delta$.

EXAMPLE 19

6-Deoxyneamine [Formula XI: Z″ is amino; A″ is hydroxyl; Q, and W‴ are hydrogen atoms and ∼ is in the $\beta$ configuration]

Refer to Chart C.

3′,4′-Di-O-acetyl-6-deoxy-1,2′,3,6′-tetrakis-N-(trifluoroacetyl)-neamine (X, Example 16, 1.073 g.) and sodium hydroxide (690 mg.) in methanol (8.5 ml.) and water (8.5 ml.) are refluxed for 15 minutes and cooled. Hydrochloric acid (1 N, 9 ml.) and water (40 ml.) are added. This mixture is passed over an Amberlite® CG-50 ion exchange resin (100-200 mesh) in the ammonium form. The column is washed with water (50 ml.) and then eluted with a gradient of water (100 ml.) and ammonium hydroxide (0.5 N, 100 ml.) followed by a gradient of 0.5 N ammonium hydroxide (100 ml.) and 2 N ammonium hydroxide (100 ml.). Homogeneous one-spot fractions are pooled and lyophilized to give the title compound. CMR ($D_2O$) 41.47, 42.10, 43.07, 46.13, 51.14, 56.61, 72.58, 72.77, 74.39, 74.97, 91.32, and 102.51$\delta$.

EXAMPLE 20

6-Deoxy-5-epineamine [Formula XI: Z″ is amino; A″ is hydroxyl; Q and W‴ are hydrogen atoms and ∼ is in the $\alpha$ configuration]

Refer to Chart C.

Following the general procedure of Example 19 and making non-critical variations but substituting 3′4,′-di-O-acetyl-6-deoxy-5-epi-1,2′,3,6′-tetrakis-N-(trifluoroacetyl)-neamine (X, Example 18) for 3′,4′-di-O-acetyl-6-deoxy-1,2′,3,6′-tetrakis-N-(trifluoroacetyl)-neamine the title compound is obtained.

EXAMPLE 21

6′-N-(Carbobenzoxyamino-6-deoxyneamine [Formula XII: A″ is hydroxyl; Q is a hydrogen atom; ∼ is in the $\beta$ configuration; M is —NHM′ and M′ is carbobenzoxy (—$CO_2CH_2C_6H_5$)]

Refer to Chart C.

Following the general procedures of Examples 6 and 8 of U.S. Pat. No. 3,781,268 and making non-critical variations but substituting 6-deoxyneamine (XI, Example 19) for Kanamycin A and B the title compound is obtained.

EXAMPLE 22

1-N-$\gamma$-Carbobenzoxyamino-$\alpha$-hydroxybutyryl-6′-N-carbobenzoxyamino-6-deoxyneamine [Formula XIII: A″ is hydroxyl; Q is a hydrogen atom; ∼ is in the $\beta$ configuration; M is —NHM′; M′ is carbobenzoxy and J is $\gamma$-amino-$\alpha$-hydroxybutyryl]

Refer to Chart C.

Following the general procedure of U.S. Pat. No. 3,781,268, Examples 3 and 9 and making non-critical variations but substituting 6′-N-carbobenzoxyamino-6-deoxyneamine (XII, Example 21) for the reactants in Examples 3 and 9 of U.S. Pat. No. 3,781,268 the title compound is obtained.

EXAMPLE 23

1-N-$\gamma$-Amino-$\alpha$-hydroxybutyryl-6-deoxyneamine [Formula XIV: Z″ is amino; A″ is hydroxyl; Q is a hydrogen atom; ∼ is in the $\beta$ configuration and J is $\gamma$-amino-$\alpha$-hydroxybutyryl]

Refer to Chart C.

Following the general procedure of Examples 4 and 10 of U.S. Pat. No. 3,781,268 and making non-critical variations but substituting 1-N-$\gamma$-carbobenzoxyamino-$\alpha$-hydroxybutyryl-6′-N-carbobenzoxyamino-6-deoxyneamine (XIII, Example 22) for the reactants in Examples 4 and 10 of U.S. Pat. No. 3,781,268 the title compound is obtained.

EXAMPLE 24

O-3,4-Di-O-acetyl-2,6-dideoxy-2,6-bis(trifluoroacetyl)-amino-$\alpha$-D-glucopyranosyl(1→4)-O-[4,6-di-O-acetyl-2,3-dideoxy-3-(trifluoroacetyl)amino-$\alpha$-D-arabino-hexopyranosyl(1→5)]-2,6-dideoxy-N,N′-bis(trifluoroacetyl)-D-streptamine [Formula XV: Q is a hydrogen atom; Z is a —NHE group; E is trifluoroacetyl; A′ is an —OB group; B is acetyl; W′ is E; at Ⓐ -5 ∼ is $\beta$; at Ⓒ-1 ∼ is $\alpha$; at Ⓒ-2 $R_1$ is a hydrogen atom; at Ⓒ-3 ∼ is $\beta$ and $R_1$ is —NHCOCF$_3$; m is 1; at Ⓒ-4 ∼ is $\alpha$ and $R_1$ is —O-acetyl; L is —$CH_2R_1$ and $R_1$ is —O-acetyl]

Refer to Chart D.

3′,4′-Di-O-acetyl-6-deoxy-1,2′,3,6′-tetrakis-N-(trifluoroacetyl)-neamine (X, Example 16, 1.5 g.) in ethyl acetate (25 ml.) is added to 4,6-di-O-acetyl-2,3-dideoxy-3-trifluoroacetylamido-D-arabino-hex-1-enopyranose (Example 39, 975 mg.) and boron trifluoride (1.5 ml.) in ethyl ether. After 4 hours additional sugar (487, mg.) and boron trifluoride (0.4 ml.) are added and stirred for 2 hours. The reaction mixture is diluted with ethyl acetate and methylene chloride and washed well with potassium bicarbonate. The mixture is dried and concentrated under vacuum. The residue is column chromatographed over silica gel (150 g.) eluting with chloroform-methanol (25:1). Homogeneous one-spot TLC fractions are pooled and concentrated to give the title compound. $[\alpha]_D^{25}$ +32 (methanol); CMR (acetone-$d_6$) 20.49, 35.80, 36.57, 37.66, 40.20, 45.39, 47.66, 50.39, 53.08, 63.69, 68.48, 69.64, 69.99, 70.65, 71.35, 78.71, 82.91, 96.94, 95.5, 109.82, 124.16, 138.5, 154–162, 170.28, 170.66 and 170.79$\delta$.

EXAMPLE 25

O-3,4-Di-O-acetyl-2,6-dideoxy-2,6-bis(trifluoroacetyl-) amino-$\alpha$-D-glucopyranosyl (1→4)-O-[2,3,5-triacetyl-$\beta$-D-ribofuranosyl(1→5)]-2,6-dideoxy-N,N′-bis(trifluoroacetyl)-D-streptamine [Formula XV$\beta$, at Ⓒ-1 ∼ is $\beta$] and O-3,4-di-O-acetyl-2,6-dideoxy-2,6-bis(trifluoroacetyl)amino-$\alpha$-D-glucopyranosyl(1→4)-O-[2,3,5-triacetyl-$\alpha$-D-ribofuranosyl(1→5)]-2,6-dideoxy-N,N′-bis(trifluoroacetyl)-D-streptamine [Formula XV$\alpha$, at Ⓒ-1 ∼ is $\alpha$], [Formula XV: Q is a hydrogen atom; Z′ is a —NHE group; E is trifluoroacetyl; A′ is an —OB group; B is acetyl; W′ is E; at Ⓐ -5 ∼ is $\beta$; at Ⓒ-2 and Ⓒ-3 ∼ is $\alpha$ and $R_1$ is —O—acetyl; m is 0; L is —$CH_2R_1$ and $R_1$ is —O—acetyl]

Refer to Chart D.

3′,4′-Di-O-acetyl-6-deoxy-1,2′,3,6′-tetrakis-N-(trifluoroacetyl)-neamine (X, Example 16, 2.0 g.) is mixed with benzene (35 ml.) and nitromethane (20 ml.). Benzene (15 ml.) is distilled from the mixture. A solution of 2,3,5-tri-O-acetyl-D-ribofuranosyl bromide (5.24 mm) in nitromethane (5 ml.) followed by mercuric cyanide (1.32 g.) is added to the neamine (X). The mixture is refluxed for 2 hours and monitored by TLC (chloroform-methanol, 10:1). Additional amounts of the bromide and mercuric cyanide are added at 1.5-2 hour intervals. When the reaction is complete as measured by TLC the reaction mixture is diluted with ethyl acetate, washed well with dilute acid, water and potassium carbonate. The organic diluent is removed by reduced pressure and the product chromatographed over silica gel (300 g.) eluting with chloroform-methanol (25:1). Fractions are pooled on the basis of a TLC profile, providing fractions A, B, and C. Fraction A is rechromatographed over silica gel (250 g.) eluting with chloroform-methanol (30:1). Fractions are pooled on the basis of the TLC profile as above giving fraction AA which is rechromatographed over silica gel (100 g.) eluting with ethyl acetate-SSB. Homogeneous one-spot TLC fractions are pooled and concentrated to give the title compound XV$\beta$. CMR (acetone-d$_6$) 20.43, 20.71, 36.35, 37.05, 40.32, 45.03, 50.53, 52.72, 63.48, 68.48, 69.98, 71.13, 71.35, 75.92, 78.84, 79.61, 81.41, 96.80, 107.08, 109.79, 124.16, 138.5, 156-162, 170.34, 170.58 and 171.01$\delta$; [$\alpha$]$_D$+14 (methanol).

Fraction C plus fraction AC are rechromatographed over silica gel (100 g.) eluting with ethyl acetate-SSB (1:1). Homogeneous one-spot TLC fractions are pooled and concentrated to give the title compound XV$\alpha$. CMR (acetone-d$_6$) 20.45, 20.85, 36.44, 38.24, 40.26, 45.31, 50.28, 53.06, 64.25, 67.84, 70.13, 71.34, 71.91, 77.92, 81.55, 81.97, 96.83, 103.05, 109.8, 124.2, 138.5, 156-162, 169.95, 170.47 and 170.72$\delta$.

EXAMPLE 26

O-2,6-Diamino-2,6-dideoxy-$\alpha$-D-glucopyranosyl (1→4)-O-[3-amino-2,3-dideoxy-$\alpha$-D-arabinohexopyranosyl(1→5)]-2,6-dideoxy-D-streptamine [Formula XVI: Z" is amino, A" is hydroxyl; Q and W" are hydrogen atoms; at Ⓐ -5 ~ is $\beta$; at Ⓒ -1 ~ is $\alpha$; at Ⓒ -2 R$_1$ is a hydrogen atom; at Ⓒ -3 ~ is $\beta$ and R$_1$ is amino; m is 1; at Ⓒ -4 ~ is $\alpha$; and R$_1$ is hydroxyl; L is —CH$_2$R$_1$ and R$_1$ is hydroxyl]
Refer to Chart D.

The tetraacetate (XV, Example 24, 1.0 g.) and sodium hydroxide (720 mg.) in methanol (7 ml.) and water (7 ml.) are refluxed for 12 minutes. The reaction mixture is diluted with water (45 ml.) and hydrochloric acid (1 N, 9 ml.). This mixture is passed thru an Amberlite Ⓡ CG-50 ion exchange resin (100-200 mesh) in the ammonium form. The resin is eluted with water (50 ml.), a gradient of water (200 ml.) and ammonium hydroxide (0.5 N, 200 ml.) and then with a gradient of 0.5 N ammonium hydroxide (100 ml.) and 2 N ammonium hydroxide (100 ml.). Homogeneous one-spot TLC fractions are pooled and lyophilized to give the title compound. CMR (D$_2$O) 38.42, 41.20, 41.68, 43.04, 46.00, 49.82, 52.18, 56.92, 62.20, 72.73, 73.09, 74.25, 74.40, 74.98, 82.03, 86.11, 100.37 and 100.52$\delta$.

EXAMPLE 27

O-2,6-Diamino-2,6-dideoxy-$\alpha$-D-glucopyranosyl (1→4)-O-[$\beta$-D-ribofuranosyl(1→5)]-2,6-dieoxy-D-streptamine [Formula XVI: Z" is amino; A" is hydroxyl; Q and W$\Delta$ are hydrogen atoms; at Ⓐ -5 and Ⓒ -1 ~ is $\beta$; at Ⓒ -2 and Ⓒ -3 ~ is $\alpha$ and R$_1$ is hydroxyl; m is 0; L is —CH$_2$R$_1$ and R$_1$ is hydroxyl]
Refer to Chart D.

Following the general procedure of Example 26 and making non-critical variations but substituting the pentaacetate (XV$\beta$, Example 25, 528 mg.) for the tetraacetate (XV, Example 24), there is obtained the title compound. CMR (D$_2$O) 38.57, 39.83, 42.69, 45.89, 51.77, 56.68, 63.05, 71.45, 72.64, 72.71, 73.36, 74.45, 76.11, 84.47, 85.11, 100.49, and 106.23$\delta$.

EXAMPLE 28

O-2,6-Diamino-2,6-dideoxy-$\alpha$-D-glucopyranosyl (1→4)-O-[$\alpha$-D-ribofuranosyl(1→5)]-2,6-dieoxy-D-streptamine [Formula XVI: Z" is amino; A" is hydroxyl; Q and W are hydrogen atoms; at Ⓐ -5 ~ is $\beta$; at Ⓒ -1 ~ is $\alpha$; Ⓒ -2 and Ⓒ -3 ~ is $\alpha$ and R$_1$ is hydroxyl; m is 0; L is —CH$_2$R$_1$ and R$_1$ is hydroxyl]
Refer to Chart D.

Following the general procedure of Example 26 and making non-critical variations but substituting the pentaacetate (XV$\alpha$, Example 25, 635 mg.) for the tetraacetate (XV, Example 24) there is obtained the title compound. CMR (D$_2$O) 41.36, 42.85, 45.99, 51.44, 56.52, 62.83, 70.91, 72.44, 74.09, 74.84, 82.28, 85.50, 85.94, 100.70 and 104.70$\delta$.

EXAMPLE 29

O-6-N-Carbobenzoxyamino-2,6-diamino-2,6-dideoxy-$\alpha$-D-glycopyranosyl(1→4)-O-[3-amino-2,3-didexoy-$\alpha$-D-arabinohexopyranosyl(1→5)]-2,6-dieoxy-D-streptamine [Formula XVII: A" is hydroxy; Q is a hydrogen atom; M is —NHM'; M' is carbobenzoxy; at Ⓐ -5 ~ is $\beta$; at Ⓒ -1 ~ is $\alpha$; at Ⓒ -2 R$_1$ is a hydrogen atom; at Ⓒ -3 ~ is $\beta$ and R$_1$ is amino; m is 1; at Ⓒ -4 ~ is $\alpha$ is hydroxyl; L is —CH$_2$R$_1$ and R$_1$ is hydroxyl]
Refer to Chart D.

Following the general procedure of Example 21 and making non-critical variations but using O-2,6-diamino-2,6-dideoxy-$\alpha$-D-glucopyranosyl(1→4)-O-[3-amino-2,3-dideoxy-$\alpha$-D-arabinohexopyranosyl(1→5)]-2,6-dieoxy-D-streptamine (XVI, Example 26) as the reactant the title compound is obtained.

EXAMPLES 30/31

O-6-N-Carnbobenzoxyamino-2,6-diamino-2,6-dideoxy-$\alpha$-D-glycopyranosyl(1→4)-O-[$\beta$/$\alpha$-D-ribofuranosyl(1→5)]-2,6-dieoxy-D-streptamine [Formula XVII* M is —NHM'; M' is carbobenzoxy; A" is hydroxyl; Q is a hydrogen atom; at Ⓐ -5 ~ is $\beta$; at Ⓒ -1 ~ is $\beta$/$\alpha$; at Ⓒ -2 and Ⓒ -3 ~ is $\alpha$ and R$_1$ is hydroxyl; m is 0; L is —CH$_2$R$_1$ and R$_1$ is hydroxyl]
Refer to Chart D.

Following the general procedure of Example 29 and making non-critical variations but using O-2,6-diamino-2,6-dideoxy-$\alpha$-D-glucopyranosyl(1→4)-O-[$\beta$/$\alpha$-D-ribofuranosyl(1→5)]-2,6-dieoxy-D-streptamine (XVI, Examples 27/28) as the reactants the title compounds are obtained.

EXAMPLE 32

O-1-N-$\gamma$-Carbobenzoxyamino-$\alpha$-hydroxybutyryl-6-N-carbobenzoxyamino-2,6-diamino-2,6-dideoxy-$\alpha$-D-glycopyranosyl(1→4)-O-[3-amino-2,3-dideoxy-$\alpha$-D-arabinohexopyranosyl(1→5)]-2,6-dieoxy-D-streptamine [Formula XVIII: A" is hydroxyl; Q is a hydrogen atom; M is —NHM'; M' is carbobenzoxy; J is $\gamma$-amino-$\alpha$-hydroxybutyryl; at Ⓐ -5 ~ is $\beta$; at Ⓒ -1 ~ is $\alpha$; at ©-2 R₁ is a hydrogen atom; at ©-3 ~ is β and R₁ is amino; m is 1; at ©-4 ~ is α and R₁ is hydroxyl; L is —CH₂R₁ and R₁ is hydroxyl]

Refer to Chart D.

Following the general procedure of Example 22 and making non-critical variations but using O-6-N-carbobenzoxyamino-2,6-diamino-2,6-dideoxy-α-D-glycopyranosyl(1→4)-O-[3-amino-2,3-dideoxy-α-D-arabinohexopyranosyl(1→5)]-2,6-dideoxy-D-streptamine (XVII, Example 29) as the reactant the title compound is obtained.

EXAMPLES 33/34

O-1-N-γ-Carbobenzoxyamino-α-hydroxybutyryl-6-N-carbobenzoxyamino-2,6-diamino-2,6-dideoxy-α-D-glycopyranosyl(1→4)-O-[β/α-D-ribofuranosyl(1→5)]-2,6-dideoxy-D-streptamine [Formula XVIII: M is —NHM′; M′ is carbobenzoxy; J is γ-amino-α-hydroxybutyryl; A″ is hydroxyl; Q is a hydrogen atom; at Ⓐ -5 ~ is β; at ©-1 ~ is β/α; at ©-2 and ©-3 ~ is α and R₁ is hydroxyl; m is 0; L is —CH₂R₁ and R₁ is hydroxyl]

Refer to Chart D.

Following the general procedure of Example 32 and making non-critical variations but using O-6-N-carbobenzoxyamino-2,6-diamino-2,6-dideoxy-α-D-glucopyranosyl(1→4)-O-[β/α-D-ribofuranosyl(1→5)-2,6-dideoxy-D-streptamine (XVII, Examples 30/31) as the reactants the title compounds are obtained.

EXAMPLE 35

O-1-N-γ-Amino-α-hydroxybutyryl-2,6-diamino-2,6-dideoxy-α-D-glycopyranosyl(1→4)-O-[3-amino-2,3-dideoxy-α-D-arabinohexopyranosyl (1→5)]-2,6-dideoxy-D-streptamine [Formula XIX: A″ is hydroxyl; Q is a hydrogen atom; J is γ-amino-α-hydroxybutyryl; Z″ is amino; at Ⓐ -5 ~ is β; at ©-1 ~ is α; at ©-2 R₁ is a hydrogen atom; at ©-3 ~ is β and R₁ is amino; m is 1; at ©-4 ~ is α and R₁ is hydroxyl; L is —CH₂R₁ and R₁ is hydroxyl]

Refer to Chart D.

Following the general procedure of Example 23 and making non-critical variations but using O-1-N-γ-amino-α-hydroxybutyryl-6-N-carbobenzoxyamino-2,6-diamino-2,6-dideoxy-α-D-glycopyranosyl( 1→4)-O-[3-amino-2,3-dideoxy-α-D-arabinohexopyranosyl(1→5)]-2,6-dideoxy-D-streptamine (XVIII, Example 32) as the reactant, the title compound is obtained.

EXAMPLES 36/37

O-1-N-γ-Amino-α-hydroxybutyryl-2,6-diamino-2,6-dideoxy-α-D-glycopyranosyl(1→4)-O-[β/α-D-ribofuranosyl(1→5)]-2,6-dideoxy-D-streptamine [Formula XIX: Z″ is amino; J is γ-amino-α-hydroxybutyryl; A″ is hydroxyl; Q is a hydrogen atom; at Ⓐ -5 ~ is β; at C-1 ~ is β/α; at ©-2 and ©-3 ~ is α and R₁ is hydroxyl; m is 0; L is —CH₂R₁ and R₁ is hydroxyl]

Refer to Chart D.

Following the general procedure of Example 35 and making non-critical variations but using O-1-N-γ-amino-α-hydroxybutyryl-6-N-carbobenzoxyamino-2,6-diamino-2,6-dideoxy-α-D-glucopyranosyl(1→4)-O-[β/α-D-ribofuranosyl-(1→5)]-2,6-dideoxy-D-streptamine (XVIII, Examples 33/34) as the reactants, the title compounds are obtained

EXAMPLE 38

3′,4′-Di-O-acetyl-5,6-dideoxy-5-carboethoxymethylidene-1,2′,3,6′-tetrakis-N-(trifluoroacetyl)-neamine [Formula VIII: Q and Z₁ are hydrogen atoms; Z′ is a —NHE group; E is trifluoromethyl; A′ is an —OB group; B is acetyl; W′ is E, and Z₂ is —COOC₂H₅]

Refer to Chart B.

Following the general procedure of Example 14 and making non-critical variations but substituting 3′,4′-di-O-acetyl-5,6-dideoxy-5-oxo-1,2′,3,6′-tetrakis-N-(trifluoroacetyl)-neamine (III, Example 4) for 3′,4′-di-O-p-nitrobenzoyl-5,6-dideoxy-5-oxo-1,2′,3,6′-tetrakis-N-(trifluoroacetyl)-neamine there is obtained the title compound.

Analysis: Calc'd. for $C_{28}H_{30}F_{12}N_4O_{12}$: C, 39.91; H, 3.59; N, 6.65. Found: C, 40.30; H, 3.70; N, 6.58.

EXAMPLE 39

4,6-Di-O-acetyl-2,3-dideoxy-3-trifluoroacetamido-D-arabino-hex-1-enopyranose

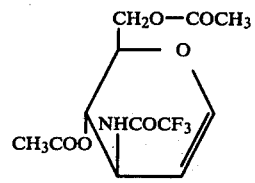

Sodium acetate (82.6 g.) is dissolved in aqueous acetic acid (50%, 340 ml.) and zinc dust (82.6 g.) is added. Cupric sulfate pentahydrate (7.44 g.) is dissolved in water and the solution is added to the zinc solution. This mixture is cooled in an ice-methanol bath.

2,4,6-Tri-O-acetyl-1-bromo-1,3-dideoxy-3-trifluoroacetamido-α-D-glucopyranose [Chem. Ber. 104, 1 (1971)] is added to the cooled mixture at 5°–15° and continued stirring for 2.5 hours at 5°. When the reaction is complete as measured by TLC (ethyl acetate-SSB, 1:2) the mixture is filtered over a pad of filter-aid and washed with methylene chloride.

The filtrate is extracted twice with methylene chloride (500 ml. each time). The organic extracts are combined, washed with water, potassium bicarbonate (5%), water again, dried and concentrated under reduced pressure to an oil (44.3 g.).

The oil (17.3 g.) is column chromatographed over silica gel (1.3 kg.) eluting with SSB-ethyl acetate (2:1). Homogeneous one-spot TLC fractions are pooled and concentrated to the title compound. TLC $R_f=0.43$ (SSB-ethyl acetate, 2:1); CMR (chloroform-$d_3$) 20.58, 49.29, 61.66, 67.64, 74.72, 99.63, 109, 121, 145.69 and 170.70.

EXAMPLE 40

3′,4′-Dideoxy-1,2′,3,6′-tetrakis-N-(trifluoroacetyl)-neamine [Formula I: Q and A′ are hydrogen atoms; Z′ is a —NHE group; E is trifluoroacetyl and W′ is E]

Following the general procedure of U.S. Pat. No. 3,996,205, Example 1 and making non-critical variations but using Gentamine $C_{1a}$ [J. Chem. Soc. (C) 3126 (1971)] as the amine there is obtained the title compound.

EXAMPLE 41

3',4'-Dideoxy-6-O-p-toluenesulfonyl-1,2',3,6'-tetrakis-N-(trifluoroacetyl)-neamine [Formula II: Q and A' are hydrogen atoms; Z' is a —NHE group; E is trifluoroacetyl; W' is E and G is p-toluenesulfonyl]

Refer to Chart A.

3',4'-Dideoxy-1,2',3,6'-tetrakis-N-(trifluoroacetyl)-neamine (I, Example 40, 10.1 g.) and p-toluenesulfonyl chloride (14.25 g.) are mixed in pyridine (100 ml.) at 20°-25° for 48 hours. A few crystals of ice are then added followed by ethyl acetate and ether. The resulting mixture is washed three times with hydrochloric acid, then water, saline and dried. Removal of the organic diluent leaves crystalline product which shows one spot on TLC chloroform:methanol (10:1) and ethyl acetate:SSB (1:1). CMR (acetone-$d_6$) 21.47, 27.93, 32.28, 44.38, 49.11, 50.47, 50.69, 68.43, 74.47, 82.29, 84.03, 99.27, 96, 110, 124, 138, 128–145 and 154–160 δ; $[\alpha]_D$ +71° (methanol).

EXAMPLE 42

3',4',5,6-Tetradeoxy-5-oxo-1,2',3,6'-tetrakis-N-(trifluoroacetyl)-neamine [Formula III: Q and A' are hydrogen atoms; Z' is a —NHE group; E is trifluoroacetyl and W' is E]

Refer to Chart A.

The p-toluenesulfonate ester (II, Example 41, 1 g.) and sodium iodide (2 g.) are heated at 100° in DMF for 20 hours. The DMF is removed by reduced pressure and the residue is dissolved in ethyl acetate-benzene-water. The organic phase is washed 3 times with water, dried and concentrated to give the product which is purified by column chromatography over silica gel. CMR (acetone-$d_6$) 23.24, 27.61, 35.91, 44.18, 45.72, 46.00, 50.49, 50.97, 67.82, 82.03, 97.25, 97.4, 109.84, 124.23, 138.6, 154–161 and 190 δ.

EXAMPLE 43

3',4',6-Trideoxy-1,2',3,6'-tetrakis-N-(trifluoroacetyl)-neamine [Formula Xβ: Q and A' are hydrogen atoms; Z is a —NHE group; E is trifluoroacetyl; W' is E and ~ is in the β configuration] and 3',4',6-trideoxy-5-epi-1,2',3,6'-tetrakis-N-(trifluoroacetyl)-neamine [Formula Xα: Q, Z, E, A' and W' are as defined above and ~ is in the α configuration]

Refer to Chart C.

A saturated solution of hydrogen chloride in THF is added dropwise to a mixture of 3',4',5,6-tetradeoxy-5-oxo-1,2',3,6'-tetrakis-N-(trifluoroacetyl)-neamine (III, Example 42, 6.8 g.), sodium cyanoborohydride (2 g.) and methyl orange (5 mg.) in THF (125 ml.) until the pink color of the indicator persists for 5 minutes. The organic diluent is removed by reduced pressure. The residue is partitioned between ethyl acetate (200 ml.), diethyl ether (100 ml.) and water (50 ml.). The organic phase is washed 3 times with hydrochloric acid (3 N), water, potassium bicarbonate and dried. The organic phase is removed under reduced pressure and the residue is column chromatographed over silica gel (500 g.) eluting with chloroform-methanol (10:1). Homogeneous fractions as measured by TLC are pooled and concentrated under reduced pressure to give the title compounds. Compound Xβ, CMR (methanol-$d_4$) 23.84, 28.39, 36.43, 39.55, 44.46, 45.71, 51.25, 51.43, 68.44, 72.56, 84.39, 99.33, 96, 110.38, 124.73, 139 and 155–162 δ. Compound Xα, CMR (methanol-$d_4$) 23.83, 28.36, 36.20, 36.88, 44.39, 48.33, 50.15, 65.18, 67.96, 78.11, and 93.84 δ.

EXAMPLE 44

O-2,3,4,6-Tetradeoxy-2,6-bis(trifluoroacetyl)-amino-α-D-glycopyranosyl(1→4)-O-[2,3,5-tri-O-acetyl-β-D-ribofuranosyl(1→5)]-2,6-dideoxy-N,N'-bis(trifluoroacetyl)-D-streptamine [Formula XVβ: Q and A' are hydrogen atoms; Z is a —NHE group; E is trifluoroacetyl; W' is E; at Ⓐ -5 ~ is β; at Ⓒ -1 ~ is β; at Ⓒ -2 and Ⓒ -3 $R_1$ is —O—acetyl and ~ is α; m is 0; L is —$CH_2R_1$ and $R_1$ is —O—acetyl] and O-2,3,4,6-tetradeoxy-2,6-bis(trifluoroacetyl)amino-α-D-glucopyranosyl(1→4)-O-[2,3,5-tri-O-acetyl-α-D-ribofuranosyl(1→5)]-2,6-dideoxy-N,N'-bis-(trifluoroacetyl)-D-streptamine [Formula XVα: Q, Z, E, A', W', Ⓐ -5, Ⓒ -2, Ⓒ -3 and L are defined above and at Ⓒ -1 ~ is α]

Refer to Chart D.

3',4',6-Trideoxy-1,2',3,6'-tetrakis-N-(trifluoroacetyl)-neamine (X, Example 43, 2 g.) is mixed with nitromethane (50 ml.) and toluene (30 ml.). The mixture is heated and 30 ml. of distillate are collected.

A mixture of 2,3,5-tri-O-acetyl-D-ribofuranosyl bromide (6.08 mmole), nitromethane (3 ml.) and mercuric cyanide (1.53 g.) are added to the distillate. The mixture is refluxed 30 min., a second addition of the bromide and mercuric cyanide is made and the mixture refluxed for 1 hour. The reaction mixture is cooled, diluted with ethyl acetate, washed with dilute hydrochloric acid, distilled water, a dilute potassium bicarbonate solution and dried. The organic diluents are removed under reduced pressure and the residue is column chromatographed over silica gel (250 g.) eluting with methylene chloride-methanol (20:1). The epimeric products are removed from faster moving impurities. The purified epimers are rechromatographed and separated by column chromatography over silica gel (250 g.) eluting with ethyl acetate-SSB (1:1) plus methanol (2%). Homogeneous one-spot TLC fractions are pooled and concentrated to give the title compounds. Compound XVβ, CMR (acetone-$d_6$) 20.40, 20.68, 23.68, 28.09, 36.16, 36.72, 44.42, 45.11, 49.63, 50.72, 64.17, 67.53, 71.32, 75.59, 78.83, 79.50, 80.73, 96.38, 106.73, 96, 109.93, 124.30, 138, 154–162, 170.33 and 170.98 δ. Compound XVα, CMR (acetone-$d_6$) 20.52, 20.41, 23.47, 27.98, 36.13, 38.14, 44.44, 45.37, 49.92, 50.40, 64.25, 66.66, 70.32, 71.81, 77.61, 81.42, 96.02, 103.07, 96, 109.91, 124.29, 136, 154–162 and 170.91 δ.

EXAMPLE 45

O-2,6-Diamino-2,3,4,6-tetradeoxy-α-D-glucopyranosyl(1→4)-O-[β-D-ribofuranosyl(1→5)]-2,6-dideoxy-D-streptamine [Formula XVI: Z" is amino; Q, A" and W'" are hydrogen atoms at Ⓐ -5 ~ is β; at Ⓒ -1 ~ is β; at Ⓒ -2 and Ⓒ -3 $R_1$ is hydroxyl and ~ is α; m is 0; L is —$CH_2R_1$ and $R_1$ is hydroxyl]

Refer to Chart D.

Following the general procedure of Example 26 and making non-critical variations but starting with O-2,3,4,6-tetradeoxy-2,6-bis(trifluoroacetyl)amino-α-D-glucopyranosyl-(1→4)-O-[2,3,5-tri-O-acetyl-β-D-ribofuranosyl(1→5)]-2,6-dideoxy-N,N'-bis(trifluoroacetyl)-D-streptamine (XVβ, Example 44), there is obtained the title compound. CMR ($D_2O$) 26.17, 28.46, 39.29, 40.83, 45.88, 51.28, 51.93, 63.08, 70.68, 71.42, 76.21, 79.65, 84.41, 85.58, 100.50 and 106.57 δ.

EXAMPLE 46

O-2,6-Diamino-2,3,4,6-tetradeoxy-α-D-glucopyranosyl(1→4)-O-[α-D-ribofuranosyl(1→5)]-2,6-dideoxy-D-streptamine [Formula XVI: Z" is amino; Q, A" and W'" are hydrogen atoms at Ⓐ -5 ~ is β; at Ⓒ -1 ~ is α; at Ⓒ -2 and Ⓒ -3 R₁ is hydroxyl and ~ is α; m is 0; L is —CH₂R₁ and R₁ is hydroxyl]

Refer to Chart D.

Following the general procedure of Example 26 and making non-critical variations but starting with O-2,3,4,6-tetradeoxy-2,6-bis(trifluoroacetyl)amino-α-D-glucopyranosyl-(1→4)-O-[2,3,5-tri-O-acetyl-α-D-ribofuranosyl(1→5)]-2,6-dideoxy-N,N'-bis(trifluoroacetyl)-D-streptamine (XVα, Example 44) there is obtained the title compound CMR (D₂O) 27.30, 28.64, 41.50, 41.76, 46.02, 51.24, 51.65, 62.83, 70.92, 71.34, 72.44, 82.38, 85.53, 86.06, 100.80 and 104.76 δ.

EXAMPLE 47

O-2,3,4,6-Tetradeoxy-2,6-bis(trifluoroacetyl)amino-α-D-glucopyranosyl(1→4)-O-[2,3,5-tri-O-acetyl-β-D-ribofuranosyl(1→5)]-2,6-dideoxy-N,N'-bis(trifluoroacetyl)-5-epi-D-streptamine [Formula XVβ: Q and A' are hydrogen atoms; Z is a —NHE group; E is trifluoroacetyl; W' is E; at Ⓐ -5 ~ is α; at Ⓒ -1 ~ is β; at Ⓒ -2 and Ⓒ -3 R₁ is —O—acetyl and ~ is α; m is 0; L is —CH₂R₁ and R₁ is —O—acetyl] and O-2,3,4,6-tetradeoxy-2,6-bis(trifluoroacetyl)amino-α-D-glucopyranosyl(1→4)-O-[2,3,5-tri-O-acetyl-α-D-ribofuranosyl(1→5)]-2,6-dideoxy-N,N'-bis-(trifluoroacetyl)-5-epi-D-streptamine [Formula XVα: Q, Z. E, A', W', Ⓐ -5, Ⓒ -2, Ⓒ -3 and L are defined above and at Ⓒ -1 ~ is α]

Refer to Chart D.

Nitromethane (10 ml.) is distilled from a mixture of 3',4',6-trideoxy-5-epi-1,2',3,6'-tetrakis-N-(trifluoroacetyl)-neamine (Xα, Example 43, 1.71 g.) in nitromethane (60 ml.). Mercuric cyanide (1.31 g.) and 2,3,5-tri-O-acetyl-D-ribofuranosyl bromide (5.2 mmoles) in nitromethane (3 ml.) is added to the hot solution. The reaction mixture is refluxed for 30 min., 2 further additions of the bromide and mercuric cyanide are made followed by 30 min. reflux in each case. When the reaction is complete as measured by TLC, chloroform-methanol (10:1), the reaction mixture is diluted with ethyl acetate (200 ml.), washed 3 times with hydrochloric acid (3 N), water, a solution of potassium bicarbonate and dried. The organic diluent is removed under reduced pressure. The residue is column chromatographed over silica gel (300 g.) using methylene chloride-methanol (20:1). A fraction free of starting material containing the epimers (XVβ and XVα) is obtained and is rechromatographed over silica gel (300 mg.) eluting with ethyl acetate-SSB (1:1) plus methanol (2%). Purification is obtained without separation of the epimers. The product fraction is chromatographed by HPLC (prepackaged silica gel) and chloroform-methanol (98:2) to give the separated epimeric products. Compound XVβ, CMR (acetone-d₆) 20.40, 20.67, 23.69, 28.21, 35.77, 35.99, 44.46, 48.22, 49.79, 64.82, 67.21, 71.50, 71.85, 75.84, 77.17, 79.74, 99.44, 106.30, 106, 109.94, 124.31, 138, 154–162, 170.33 and 171.06 δ. Compound XVα, CMR (acetone-d₆) 20.35, 20.59, 24.26, 27.95, 34.67, 36.02, 44.37, 48.25, 49.59, 64.20, 67.90, 70.60, 71.47, 73.58, 77.69, 80.64, 93.94 and 101.19.

EXAMPLE 48

O-2,6-Diamino-2,3,4,6-tetradeoxy-α-D-glucopyranosyl(1→4)-O-[β-D-ribofuranosyl(1→5)]-2,6-dideoxy-5-epi-D-streptamine [Formula XVI: Z" is amino; Q, A" and W'" are hydrogen atoms at Ⓐ -5 ~ is α; at Ⓒ -1 ~ is β; at Ⓒ -2 and Ⓒ -3 R₁ is hydroxyl and ~ is α; m is 0; L is —CH₂R₁ and R₁ is hydroxyl]

Refer to Chart D.

Following the general procedure of Example 26 and making non-critical variations but starting with O-2,3,4,6-tetradeoxy-2,6-bis(trifluoroacetyl)amino-α-D-glucopyranosyl-(1→4)-O-[2,3,5-tri-O-acetyl-β-D-ribofuranosyl(1→5)]-2,6-dideoxy-N,N'-bis(trifluoroacetyl)-5-epi-D-streptamine (XVβ, Example 47) the title compound is obtained. CMR (D₂O) 27.35, 28.71, 38.85, 41.21, 44.52, 45.97, 48.68, 50.84, 64.48, 70.90. 72.20, 75.64; 76.14, 81.10, 84.16, 97.05, and 109.89 δ.

EXAMPLE 49

O-2,6-Diamino-2,3,4,6-tetradeoxy-α-D-glucopyranosyl(1→4)-O-[α-D-ribofuranosyl(1→5)]-2,6-dideoxy-5-epi-D-streptamine [Formula XVI: Z" is amino; Q, A" and W'" are hydrogen atoms at Ⓐ -5 ~ is α; at Ⓒ -1 ~ is α; at Ⓒ -2 and Ⓒ -3 R₁ is hydroxyl and ~ is α; m is 0; L is —CH₂R₁ and R₁ is hydroxyl]

Refer to Chart D.

Following the general procedure of Example 26 and making non-critical variations but starting with O-2,3,4,6-tetradeoxy-2,6-bis(trifluoroacetyl)-α-D-glucopyranosyl-(1→4)-O-[2,3,5-tri-O-acetyl-α-D-ribofuranosyl(1→5)]-2,6-dideoxy-N,N'-bis(trifluoroacetyl)-5-epi-D-streptamine (XVα, Example 47) the title compound is obtained. CMR (acetone-d₆) 26.94, 28.69, 36.21, 41.26, 44.02, 46.02, 48.48, 50.78, 62.77, 71.32, 72.52, 73.08, 83.25, 85.36, 99.35 and 100.89 δ.

We claim:

1. A compound of the formula:

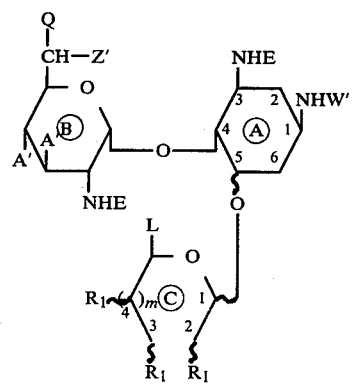

XV or a pharmaceutically acceptable salt thereof where R₁ is selected from the group consisting of hydrogen, hydroxy, —O—acetyl, —O—benzyl, —O—benzoyl, —NHR₂, —NR₂R₃; where R₂ is hydrogen, acetyl, or trifluoroacetyl; where R₃ is alkyl of 1 thru 4 carbon atoms; wheren m is zero or 1; where L is —CH₂R₁ or

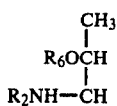

with the proviso that when L is

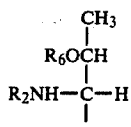

m is 1 and $R_1$ is acetyl; where Q is a hydrogen atom or methyl group; Z' is —NHE, —OB or —NCH$_3$E; where E is a removable amino blocking group; where B is a removable alcohol blocking group; where A' is a hydrogen atom or —OB group; where W' is E or J; where J is an alkyl group of 1 thru 3 carbon atoms or

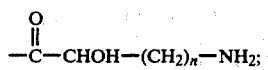

where n is 0 thru 2 and where ∼ indicates the attached substituent is in either the α or β configuration.

2. A compound according to claim 1 where A' is an —OB group and B is acetyl or p-nitrobenzoyl.

3. A compound according to claim 1 where Q is a hydrogen atom, Z' is a —NHE group, W' is E and E is trifluoroacetyl.

4. A compound according to claim 3 where Ⓒ is selected from the group consisting of glucose, ribose, 3-aminoglucose and 3-aminoribose.

5. A compound according to claim 4 which is O-3,4-di-O-acetyl-2,6-dideoxy-2,6-bis(trifluoroacetyl)-amino-α-D-glucopyranosyl(1→4)-O-[4,6-di-O-acetyl-2,3-dideoxy-3-(trifluoroacetyl)amino-α-D-arabinohex-opyranosyl(1→5)]-2,6-dideoxy-N,N'-bis(trifluoroacetyl)-D-streptamine.

6. A compound according to claim 4 which is O-3,4-di-O-acetyl-2,6-dideoxy-2,6-bis(trifluoroacetyl)amino-α-D-glucopyranosyl(1→4)-O-[2,3,5-tri-O-acetyl-β-ribofuranosyl(1→5)]-2,6-dideoxy-N,N'-bis-(trifluoroacetyl)-D-streptamine.

7. A compound according to claim 4 which is O-3,4-di-O-acetyl-2,6-dideoxy-2,6-bis(trifluoroacetyl)amino-α-D-glucopyranosyl(1→4)-O-[2,3,5-triacetyl-α-D-ribofuranosyl(1→5)]-2,6-dideoxy-N,N'-bis(trifluoroacetyl)-D-streptamine.

8. A compound of the formula:

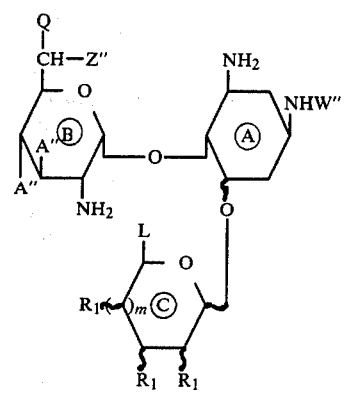

or a pharmaceutically acceptable salt thereof where Z" is amino, hydroxyl or methyl amino; where A" is a hydrogen atom or hydroxyl group; where W" is J or a hydrogen atom and where $R_1$, m, L, Q, ∼ and J are defined in claim 1.

9. A compound according to claim 8 where A" is hydroxyl, Z" is amino, and W" and Q are hydrogen atoms.

10. A compound according to claim 9 where Ⓒ is selected from the group consisting of glucose, ribose, 3-aminoglucose and 3-aminoribose.

11. A compound according to claim 10 which is O-2,6-diamino-2,6-dideoxy-α-D-glucopyranosyl(1→4)-O-[3-amino-2,3-dideoxy-α-D-arabinohex-opyranosyl(1→5)]-2,6-dideoxy-D-streptamine.

12. A compound according to claim 10 which is O-2,6-diamino-2,6-dideoxy-α-D-glucopyranosyl(1→4)-O-[β-D-ribofuranosyl(1→5)]-2,6-dideoxy-D-streptamine.

13. A compound according to claim 10 which is O-2,6-diamino-2,6-dideoxy-α-D-glucopyranosyl(1→4)-O-[α-D-ribofuranosyl(1→5)]-2,6-dideoxy-D-streptamine.

14. A compound of the formula:

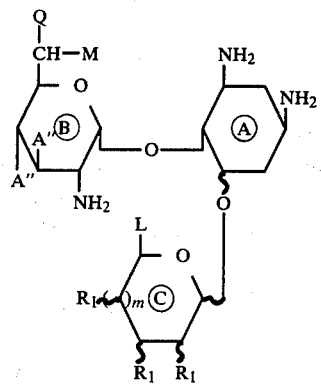

or a pharmaceutically acceptable salt thereof where A" is a hydrogen atom or hydroxyl group; where M is —NHM', —NCH$_3$M' or hydroxyl; where M' is a removable selective amino blocking group and where Q, ∼, $R_1$, m and L are defined in claim 1.

15. A compound according to claim 14 where Q is a hydrogen atom and A" is hydroxyl.

16. A compound according to claim 15 where Ⓒ is selected from the group consisting of glucose, ribose, 3-aminoglucose and 3-aminoribose.

17. A compound according to claim 16 which is O-6-N-carbobenzoxyamino-2,6-diamino-2,6-dideoxy-α-D- glucopyranosyl-(1→4)-O-[3-amino-2,3-dideoxy-α-D-arabinohexopyranose-(1→5)]-2,6-dideoxy-D-streptamine.

18. A compound according to claim 16 which is O-6-N-carbobenzoxyamino-2,6-diamino-2,6-dideoxy-α-D-glucopyranosyl-(1→4)-O-[β-D-ribofuranosyl(1→5)]-2,6-dideoxy-D-streptamine.

19. A compound according to claim 16 which is O-6-N-carbobenzoxyamino-2,6-diamino-2,6-dideoxy-α-D-glucopyranosyl(1→4)-O-[α-D-ribofuranosyl(1→5)]-2,6-dideoxy-D-streptamine.

20. A compound of the formula:

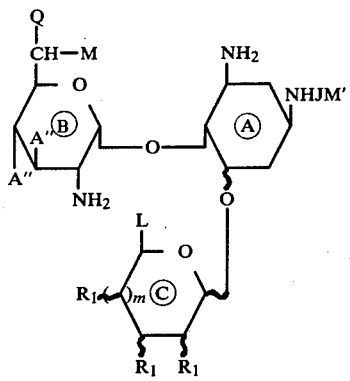

XVIII or a pharmaceutically acceptable salt thereof where A" is a hydrogen atom or hydroxyl group; where M is —NHM', —NCH₃M' or hydroxyl; where M' is a removable selective amino blocking group and where Q, J, ∼, R₁, m and L are defined in claim 1.

21. A compound according to claim 20 where Q is a hydrogen atom and A" is hydroxyl.

22. A compound according to claim 20 where Ⓒ is selected from the group consisting of glucose, ribose, 3-aminoglucose, and 3-aminoribose.

23. A compound according to claim 22 which is O-1-N-γ-carbobenzoxyamino-α-hydroxybutyryl-6-N-carbobenzoxyamino-2,6-diamino-2,6-dideoxy-α-D-glycopyranosyl(1→4)-O-[3-amino-2,3-dideoxy-α-D-arabinohexopyranosyl(1→5)]-2,6-dideoxy-D-streptamine.

24. A compound according to claim 22 which is O-1-N-γ-carbobenzoxyamino-α-hydroxybutyryl-6-N-carbobenzoxyamino-2,6-diamino-2,6-dideoxy-α-D-glucopyranosyl(1→4)-O-[β-D-ribofuranosyl(1→5)]-2,6-dideoxy-D-streptamine.

25. A compound according to claim 22 which is O-1-N-γ-carbobenzoxyamino-α-hydroxybutyryl-6-N-carbobenzoxyamino-2,6-diamino-2,6-dideoxy-α-D-glucopyranosyl(1→4)-O-[α-D-ribofuranosyl(1→5)]-2,6-dideoxy-D-streptamine.

26. A compound of the formula:

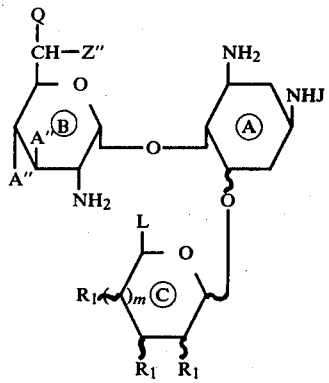

XIX or a pharmaceutically acceptable salt thereof where Z" is an amino, hydroxyl or methylamino group; where A" is a hydrogen atom or hydroxyl group and where Q, J, ∼, R₁, m and L are defined in claim 1.

27. A compound according to claim 26 where Q is a hydrogen atom, Z" is amino and A" is hydroxyl.

28. A compound according to claim 27 where Ⓒ is selected from the group consisting of glucose, ribose, 3-aminoglucose and 3-aminoribose.

29. A compound according to claim 28 which is O-1-N-γ-amino-α-hydroxybutyryl-2,6-diamino-2,6-dideoxy-α-D-glucopyranosyl(1→4)-L-[3-amino-2,3-dideoxy-α-D-arabinohexopyranosyl(1→5)]-2,6-dideoxy-D-streptamine.

30. A compound according to claim 28 which is O-1-N-γ-amino-α-hydroxybutyryl-2,6-diamino-2,6-dideoxy-α-D-glucopyranosyl(1→4)-O-[β-D-ribofuranosyl(1→5)]-2,6-dideoxy-D-streptamine.

31. A compound according to claim 28 which is O-1-N-γ-amino-α-hydroxybutyryl-2,6-diamino-2,6-dideoxy-α-D-glucopyranosyl(1→4)-O-[α-D-ribofuranosyl(1→5)]-2,6-dideoxy-D-streptamine.

32. A compound according to claim 1 where A' is a hydrogen atom.

33. A compound according to claim 32 which is O-2,3,4,6-tetradeoxy-2,6-bis(trifluoroacetyl)amino-α-D-glucopyranosyl(1→4)-O-[2,3,5-tri-O-acetyl-β-D-ribofuranosyl(1→5)]-2,6-dideoxy-N,N'-bis(trifluoroacetyl)-D-streptamine.

34. A compound according to claim 32 which is O-2,3,4,6-tetradeoxy-2,6-bis(trifluoroacetyl)amino-α-D-glucopyranosyl(1→4)-O-[2,3,5-tri-O-acetyl-α-D-ribofuranosyl(1→5)]-2,6-dideoxy-N,N'-bis(trifluoroacetyl)-D-streptamine.

35. A compound according to claim 32 which is O-2,3,4,6-tetradeoxy-2,6-bis(trifluoroacetyl)amino-α-D-glucopyranosyl(1→4)-O-[2,3,5-tri-O-acetyl-β-ribofuranosyl(1→5)]-2,6-dideoxy-N,N'-bis(trifluoroacetyl)-5-epi-D-streptamine.

36. A compound according to claim 32 which is O-2,3,4,6-tetradeoxy-2,6-bis(trifluoroacetyl)amino-α-D-glucopyranosyl(1→4)-O-[2,3,5-tri-O-acetyl-α-D-ribofuranosyl(1→5)]-2,6-dideoxy-N,N'-bis(trifluoroacetyl)-5-epi-D-streptamine.

37. A compound according to claim 8 where A" is a hydrogen atom.

38. A compound according to claim 37 which is O-2,6-diamino-2,3,4,6-tetradeoxy-α-D-glucopyranosyl(1→4)-O-[β-D-ribofuranosyl(1→5)]-2,6-dideoxy-D-streptamine.

39. A compound according to claim 37 which is O-2,6-diamino-2,3,4,6-tetradeoxy-α-D-glucopyranosyl(1→4)-O-[α-D-ribofuranosyl(1→5)]-2,6-D-streptamine.

40. A compound according to claim 37 which is O-2,6-diamino-2,3,4,6-tetradeoxy-α-D-glucopyranosyl(1→4)-O-[β-D-ribofuranosyl(1→5)]-2,6-dideoxy-5-epi-D-streptamine.

41. A compound according to claim 37 which is O-2,6-diamino-2,3,4,6-tetradeoxy-α-D-glucopyranosyl(1→4)-O-[α-D-ribofuranosyl(1→5)]-2,6-dideoxy-5-epi-D-streptamine.

* * * * *